(12) United States Patent
Akgun

(10) Patent No.: US 6,806,712 B2
(45) Date of Patent: Oct. 19, 2004

(54) MAGNETIC RESONANCE IMAGING APPARATUS AND METHOD

(75) Inventor: Ali Akgun, Middlesex (GB)

(73) Assignee: Specialty Magnetics Limited, Northolt (GB)

( * ) Notice: Subject to any disclaimer, the term of this patent is extended or adjusted under 35 U.S.C. 154(b) by 0 days.

(21) Appl. No.: 10/239,152

(22) PCT Filed: Mar. 22, 2001

(86) PCT No.: PCT/GB01/01268
§ 371 (c)(1),
(2), (4) Date: Dec. 24, 2002

(87) PCT Pub. No.: WO01/70109
PCT Pub. Date: Sep. 27, 2001

(65) Prior Publication Data
US 2003/0094947 A1 May 22, 2003

(30) Foreign Application Priority Data
Mar. 22, 2000 (GB) .............................................. 0007018

(51) Int. Cl.7 ............................................... G01V 3/00
(52) U.S. Cl. ..................................... 324/318; 324/309
(58) Field of Search ............................... 324/318, 309, 324/307, 311, 320, 322; 128/653

(56) References Cited

U.S. PATENT DOCUMENTS

| | | | | |
|---|---|---|---|---|
| 4,490,675 A | 12/1984 | Knuettel et al. | ............ | 324/319 |
| 4,652,824 A | 3/1987 | Oppelt | ........................ | 324/318 |
| 4,658,229 A | 4/1987 | Chen et al. | .................. | 324/318 |
| 4,701,736 A | 10/1987 | McDougall et al. | ........ | 324/319 |
| 4,812,797 A | 3/1989 | Jayakumar | ................... | 324/318 |
| 4,862,087 A | 8/1989 | Hillenbrand et al. | ........ | 324/319 |
| 4,875,485 A * | 10/1989 | Matsutani | .................... | 600/415 |
| 5,428,292 A | 6/1995 | Dorri et al. | .................. | 324/318 |
| 5,498,961 A | 3/1996 | Kuhn et al. | .................. | 335/299 |
| 5,570,073 A | 10/1996 | Muller | ........................ | 324/319 |
| 5,596,303 A * | 1/1997 | Akgun et al. | ................ | 335/216 |
| 5,735,278 A | 4/1998 | Hoult et al. | ................. | 324/318 |
| 6,611,703 B2 * | 8/2003 | Kuth et al. | .................. | 600/415 |

FOREIGN PATENT DOCUMENTS

| | | |
|---|---|---|
| EP | 0 359 374 A1 | 3/1990 |
| EP | 0 654 675 A1 | 5/1995 |
| EP | 0 679 900 A1 | 11/1995 |
| GB | 2 285 313 A | 7/1995 |
| WO | WO 94/06034 A | 3/1994 |
| WO | WO 96/08199 A | 3/1996 |
| WO | WO 98/00726 A1 | 1/1998 |

OTHER PUBLICATIONS

C. Minas et al.—"Structural Design and Analysis of a Cryogen–Free Open Superconducting Magnet for Interventional MRI Applications," IEEE Transaction on Applied Superconductivity, vol. 5, No. 2, Jun. 1995, pp. 173–174.

* cited by examiner

Primary Examiner—Brij B. Shrivastav
(74) Attorney, Agent, or Firm—Dickstein Shapiro Morin & Oshinsky LLP

(57) ABSTRACT

A magnetic resonance imaging assembly for generating a substantially homogenous magnetic field within an imaging-field-zone to produce an image of a region (anatomy-of-interest (2)) in a patient (1) comprises a bore into which the region of the patient can be placed, and a plurality of coaxially arranged coils (30a, b, c, d) surrounding the bore. The coils are arranged to generate a substantially homogenous magnetic field in the imaging-field-zone in the bore. The bore has a diameter (38) substantially larger than the axial length (39) of the bore. The large bore enables any region of the patient to be imaged to be placed in the region of highest homogeneity within the imaging field zone (11) and provides for access to the region of the patient being imaged to a health-care professional (5) during the imaging process.

28 Claims, 16 Drawing Sheets

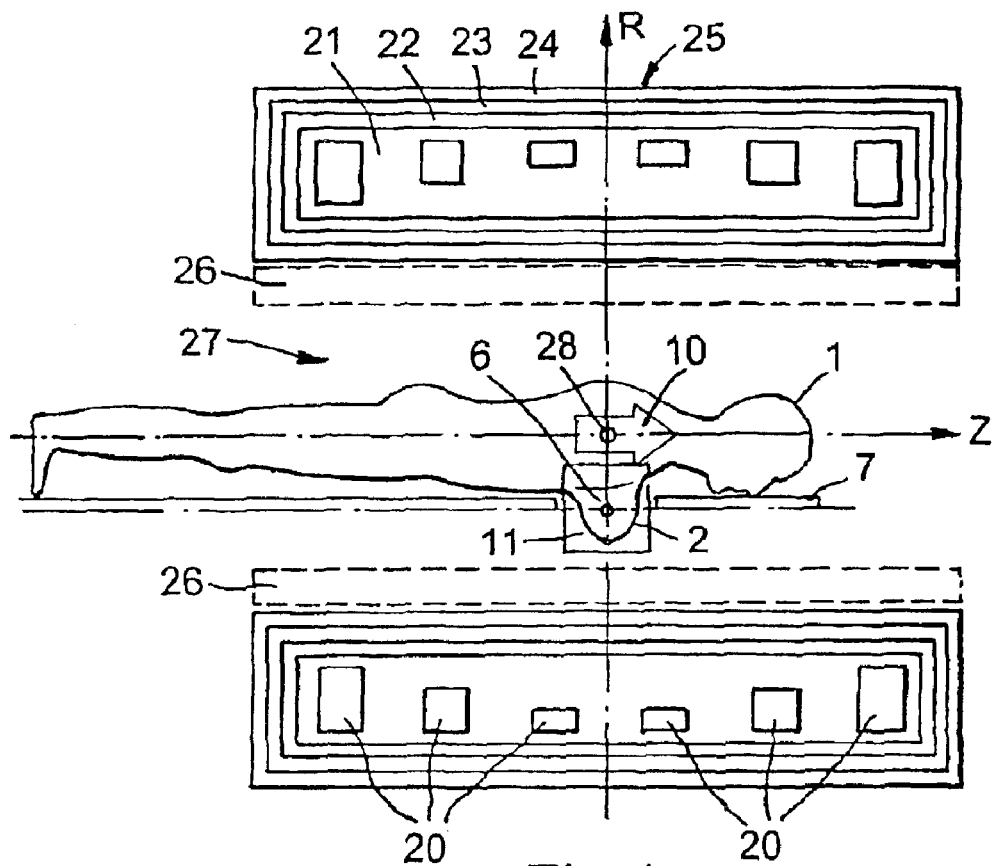
Fig.1a
PRIOR ART
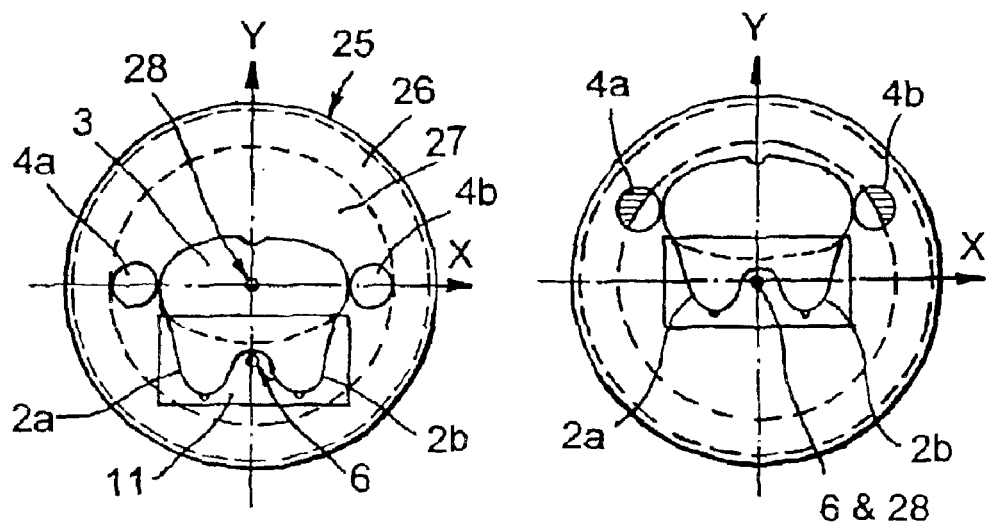
Fig.1b
PRIOR ART
Fig.1c
PRIOR ART

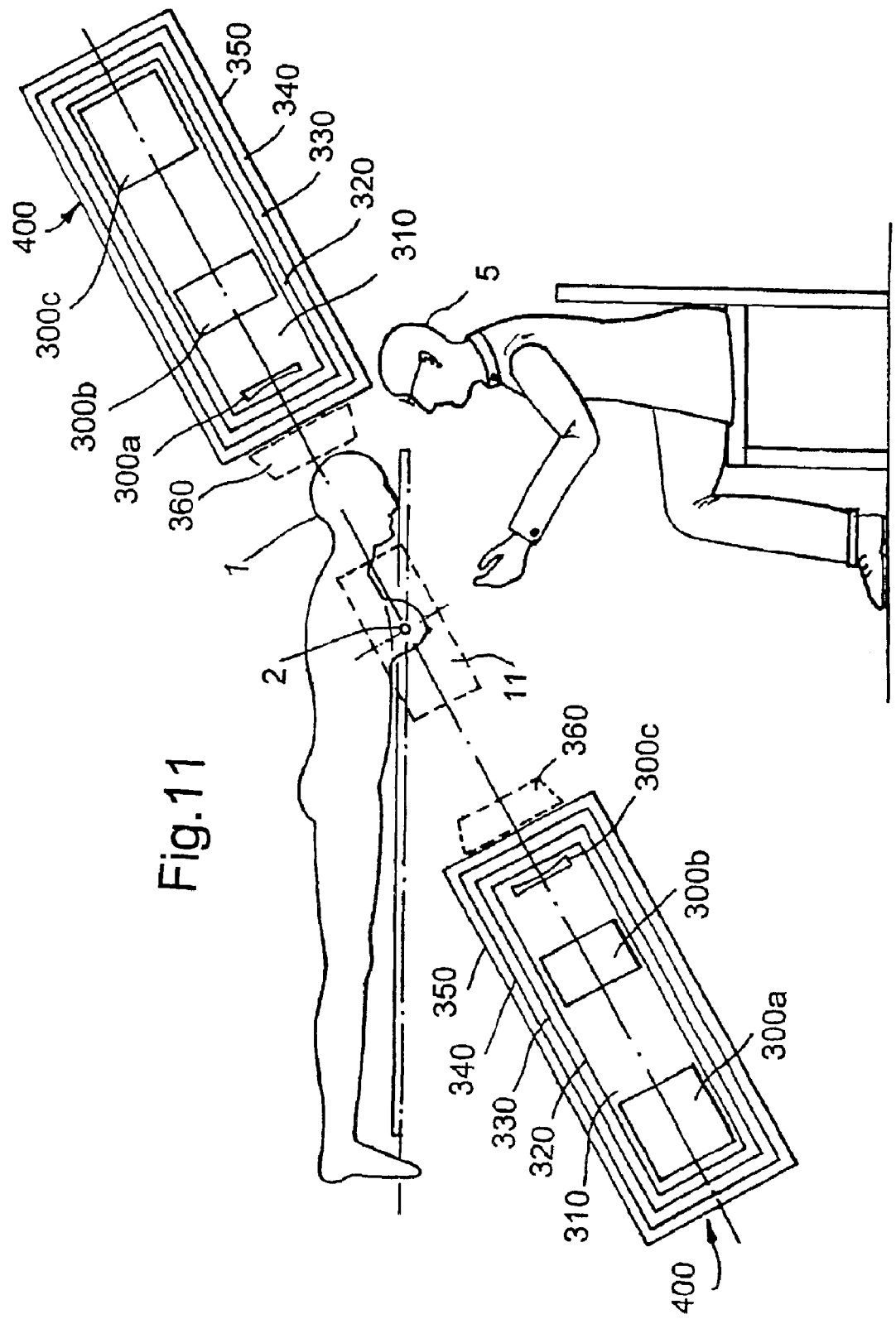

MAGNETIC RESONANCE IMAGING APPARATUS AND METHOD

The present invention generally relates to a magnetic resonance (MR) imaging apparatus and method for generating a substantially homogenous static magnetic field within a desired spatial region. More particularly the present invention relates to the magnetic resonance imaging of a desired region of a human body ("anatomy of interest").

Magnetic resonance imaging relies on the availability of a uniform, homogenous, static magnetic field. In order to image an "anatomy-of-interest" (e.g. chest, head or female breast etc.) it needs to be placed within the substantially homogenous zone of the static magnetic field generated by the magnet assembly of the overall magnetic resonance imaging apparatus. This zone of the magnetic field which is used in the magnetic resonance imaging will be referred to as the "imaging-field-zone".

Since the quality of the MR image is very dependent upon the degree of homogeneity achieved within the imaging-field-zone, a great deal of time and effort is devoted to the design and optimisation of MR imaging magnets to achieve this. As schematically depicted in FIG. 1a, the main objective of the magnet designer is to design a magnet which generates a static magnetic flux density vector 10;

$$B(x,y,z) = B_x i + B_y j + B_z k \quad (Eq. 1)$$

over the imaging-field-zone which is directed substantially along a single axis only (e.g. the z axis in FIG. 1a where B (0,0, z)=$B_z k$). In Equation 1 above, the vectoral quantities are printed in bold letters and the i, j and k represent 'unit vector' quantities along the x-axis, y-axis and z-axis, respectively. Furthermore, it can be shown that the $B_z$ component (magnitude of the B vector) can be expressed in the form of;

$$B_z = B_0 + B_1 + B_{+2} + B_3 + \ldots + B_n \quad (Eq. 2)$$

where the terms "$B_1 + B_{+2} + B_3 + \ldots + B_n$" are collectively referred to as "error terms" or "residuals". The ultimate objective of the magnet designer, during the design process, is to get rid of as many of the "error terms" as possible in order to achieve the ultimate goal of;

$$B_z = B_0 \quad (Eq. 3)$$

However, in practice it is not always possible to obtain the same degree of homogeneity within every point of a given imaging field-zone. This will be explained with reference to FIG. 1a which is a schematic, longitudinal section of a prior-art magnet (conventional, six-coil, cylindrical, narrow-bore, axially-long) assembly. A lateral view of the patient is also included. Conventionally, the patient 1 is arranged to lie on a patient-positioner 7 which is parallel to the z-axis of the magnet. The conventional whole body scanner magnet assembly comprises a low temperature chamber 21 operating at around 4° K (i.e. liquid helium temperature). Superconductive low temperature coils 20 are arranged within the chamber 21. A thermal radiation shield 22 is arranged around the chamber 21 and around the radiation shield 22 is arranged a high temperature chamber 23 operating at 77K (i.e. liquid nitrogen temperature). Surrounding the high temperature chamber 23 is a vacuum chamber 24. Within the bore of the magnet of the assembly there is provided an arrangement 26 of room temperature shims, gradient coils and radio frequency (RF) coils.

The general purpose, conventional, whole-body MR imaging systems are designed with the objective of being able to image effectively all parts of the human anatomy by using the centre of the thorax as reference-point 28 (i.e. x=0, y=0 and z=0). They are designed as axially symmetric structures. The magnet design process involves the selection of the number of superconductive coils 20, their axial and radial locations, the magnitude of the current flowing through the coils, the number of turns, etc. When all these parameters are 'optimally' selected, then a substantially homogenous magnetic field within an imaging-field-zone, which is centred at the geometrical centre 28 of the magnet assembly, may be generated. However, although the magnet designer can achieve theoretically possible maximum homogeneity (i.e. $B_z = B_0$) at the geometrical centre 28 of the magnet, inherently the same maximum homogeneity can not be achieved at other spatial locations. In other words, as schematically illustrated in FIGS. 2a and 2b, although the field is "pure" at the geometrical centre 28 of the magnet, the degree of homogeneity decreases gradually at increasing distances away from the geometrical centre 28. Figuratively speaking, for example the homogeneity calculated in a, say, 10 cm diameter imaging-field-zone is much better that the homogeneity calculated for much larger imaging-field-zones (e.g. say 20 cm, 30 cm etc, diameter zones). This is schematically depicted in FIGS. 2a and 2b where the most homogenous zone within the magnet's bore 27 is zone 12a (i.e. zone with the smallest diameter). The homogeneity calculated for the zones 12b, 12c and 12d is increasingly much lower that the homogeneity calculated for zone 12a.

Now, let us assume the anatomy-of-interest which needs to be imaged, with a prior art, conventional whole body MR scanner, is female breast. More specifically, as depicted in FIGS. 1a, 1b and 1c, the anatomy-of-interest 2 comprises the left-breast 2a and the right breast 2b of the patient 1. It can be seen that the centre 6 of the anatomy-of-interest is not at the geometrical centre 28 of the magnet assembly. This means that the area 11 of the anatomy-of-interest does not lie within the available most homogenous zones of the magnet's imaging-field. Referring now to FIGS. 1b and 1c, if one attempts to position the centre of the breast 6 at the geometrical centre of the whole body magnet 28 by lifting the patient upwards, in majority of the cases, this is not permitted by the narrower bore size of the magnet. As illustrated in FIG. 1c, this would not be possible since the arms 4a and 4b of the patient 1 would be required to lie within the regions provided for the room temperature shim coils, gradient coils and RF coils 26 in a conventional whole body scanner. For this reason, one could argue that the breast images obtained by a whole body scanner is not always optimal, since they are not always imaged by making use of the most homogeneous magnetic field available.

Unfortunately, at present, the clinical application of breast MR imaging is restricted to conventional, general purpose, whole body scanners (e.g. figure 1a), and the breast referral cases have to compete for scanner time with many other cases of referrals. The design of the conventional 'whole body' scanners tend to encapsulate the patient and only permit limited access to patient by the health care professionals and make the task of performing interventional procedures more complicated and difficult. Interventional radiologists and surgeons require:

(a) totally 'open-access' to breast and patient;
(b) easy 'image-guided' diagnostic procedure (fine needle aspiration, core biopsy etc.);
(c) easy 'image-guided' surgical treatment (e.g. lumpectomy) and other therapeutic procedures (e.g. tumour ablation using laser, rf, microwave, focused ultrasound energies, etc.).

The whole body cylindrical magnet based MR scanners (see FIG. 1a) does not allow the direct interactive placements of interventional devices (e.g. biopsy needles and optical/laser fibres used for thermal ablation of tumours) into the breast. They require the withdrawal of the patient from the bore of the magnet in order to gain access to the breast. This together with the possible movement of the patient may result in the imprecise insertion and localisation of the interventional devices.

Furthermore, in addition to the problem of patient inaccessibility within the bore of the conventional whole body scanner, the claustrophobic nature of the design due to patient encapsulation is also a factor affecting patient-acceptance rate of whole body scanners. All of these limit the widespread use and the exploitation of the full potential MR modality in the overall management of patients, in particular the patients with breast cancer.

One attempt to reduce the problem of patient encapsulation is described in U.S. Pat. No. 4,701,736, the content of which is hereby incorporated by reference. This patent discloses a so-called planar magnet design in which the axial length of the magnet assembly is reduced. This reduction in axial length reduces patient encapsulation. However, here, the motivation is to replace the conventional, solenoidal, axially long magnet with a shorter magnet but the narrow bore size still kept the same. This patent also discloses magnetic arrangements where the imaging-field-zone is projected outside the bore of the magnet to avoid any encapsulation at all.

A similar technique is disclosed in UK Patent No. 2285313 and U.S. Pat. No. 5,596,303, the contents of which are hereby incorporated by reference. In these patents an improved magnet assembly is provided which uses close-in high temperature superconducting correction coils to provide the required homogenous field within the bore of the magnet or extending beyond the bore of the magnet. This arrangement provides a similar benefit of reduced patient encapsulation as provided by the arrangement of the U.S. Pat. No. 4,701,736.

The problem of patient encapsulation is also considered in International patent publication WO 94/06034. The arrangement discloses a frustoconical magnetic resonance imaging magnet assembly which provides a large opening to allow a healthcare professional access to the patient. Further, the patient can be inclined relatively within the frustoconical magnetic assembly to further enhance patient accessibility. Although this reduces the degree of patient encapsulation, it requires a large magnetic assembly having a large axial length.

Further attempt to reduce patient encapsulation while still providing whole body scanning is disclosed in International patent publication WO 98/00726. In this arrangement a toroidal shaped magnetic assembly is used to form a sequence of cross-section images of an object and to form a complete image of the object by scanning.

The present invention provides an improved magnetic resonance imaging technique for imaging a region of a patient which requires a minimum patient encapsulation and which provides a large bore, axially short magnet which enables the patient and the magnet to be relatively positioned in three dimensions and/or in relative inclination to enable the desired region of a patient to be positioned at the most homogenous region of the magnetic field within the bore of the magnet. The positioning of the centre of the anatomy of interest to be imaged of the patient at the centre of the region of homogeneity i.e. at the region of highest homogeneity, ensures an image of the highest fidelity will be produced.

Thus in accordance with the first aspect of the present invention a magnetic resonance imaging magnet assembly has a bore large enough to enable any part of the patient to be placed on the axis of the bore at which the imaging-field-zone is centred and has the highest homogeneity. In the present invention either the patient can be manoeuvred in three dimensions within the bore, or the magnet assembly can be moved three dimensionally relative to the patient to provide the relative positioning. An added advantage of the large bore of the magnet assembly is that there is a minimum patient encapsulation and healthcare professionals are provided with good access to the region of the patient being imaged.

In the prior art axially short magnet based magnetic resonance imaging systems, although there is some improvement to the accessibility of the patient, the size of the bore is insufficient to enable all regions of the patient to be imaged to be placed within the most homogeneous region. In this aspect of the present invention, because of the large bore provided by the magnet assembly, it is possible to image any body part of the patient within the most homogeneous zone of the imaging-field-zone.

In one embodiment of the present invention, the bore of the magnet has a diameter which is preferably larger than twice the length measured between the iso-centre of the breast of an average height female and the tip of her head. The bore diameter is, in one preferred embodiment, at least 110 cms. In one preferred embodiment the axial length of the bore is less than 40 cms. Thus in one preferred embodiment of the present invention the ratio of the diameter to the axial length is at least 1.5.

In another aspect of the present invention there is provided a magnetic resonance imaging technique in which a patient is positioned in the bore of a large bore magnet so that the patient is inclined relative to the axis of the magnet assembly so that a desired slice of the anatomy-of-interest of the patient that is to be imaged is positioned in a prefered imaging plane within the imaging-field-zone of the magnet assembly. The ability to relatively incline the patient and the magnet assembly enables a health care professional to obtain an image of a desired slice of the anatomy-of-interest of high quality because of positioning of the slice of the anatomy-of-interest an imaging-plane of highest homogeneity within the imaging-field-zone.

Thus in accordance with this aspect of the present invention, the large size of the bore enables a patient to be imaged in an inclined position within the bore of the magnet to enable a healthcare professional to select the direction of the imaging-plane to coincident with the desired slice of the anatomy-of-interest to be imaged.

In a preferred embodiment of the present invention a patient is placed in the bore of the magnet and then relative rotation between the patient and the magnet assembly takes place such that the patient is relatively rotated in 3D (three dimensions) in the bore about a pivot point on the axis at the geometric centre of the bore, whilst maintaining the anatomy of the interest of the patient in the imaging field zone of the magnet assembly. Thus, in accordance with this embodiment of the present invention, a healthcare professional can select the angle of inclination and in one embodiment of the present invention, more than one image can be taken at different angles of inclination with the anatomy-of-interest of the patient being kept centred on the centre of the imaging-field-zone having the highest homogeneity.

Thus in accordance with this aspect of the present invention, the relative inclination of the patient and the magnet assembly provides the benefit of enabling the healthcare professional to select the angle of the image plane in the anatomy-of-interest of the patient, and provides the healthcare professional with a greater accessibility to the region of the patient being imaged.

Embodiments to the present invention will now be described with reference to the accompanying drawings, in which:

FIG. 1a is a schematic longitudinal section of a prior art magnet assembly and a lateral view of the patient illustrating the displacement between the centre of the anatomy of interest and the geometrical centre of the magnet assembly;

FIG. 1b is a schematic cross sectional view of the prior art magnet depicted in FIG. 1a;

FIG. 1c is a schematic cross sectional view of the prior art magnet assembly depicted in FIGS. 1a and 1b illustrating an attempt to relocate the centre of the anatomy-of-interest to be coincident with the geometrical centre of the magnet;

FIG. 11 is a schematic longitudinal sectional view of a seventh embodiment of the present invention wherein the magnet assembly is of rectangular cross section and is inclined relative to a prone patient;

FIG. 12b is a diagram illustrating an arrangement for rotation of the magnet assembly in the method illustrated in FIG. 12a;

Figure 2A:
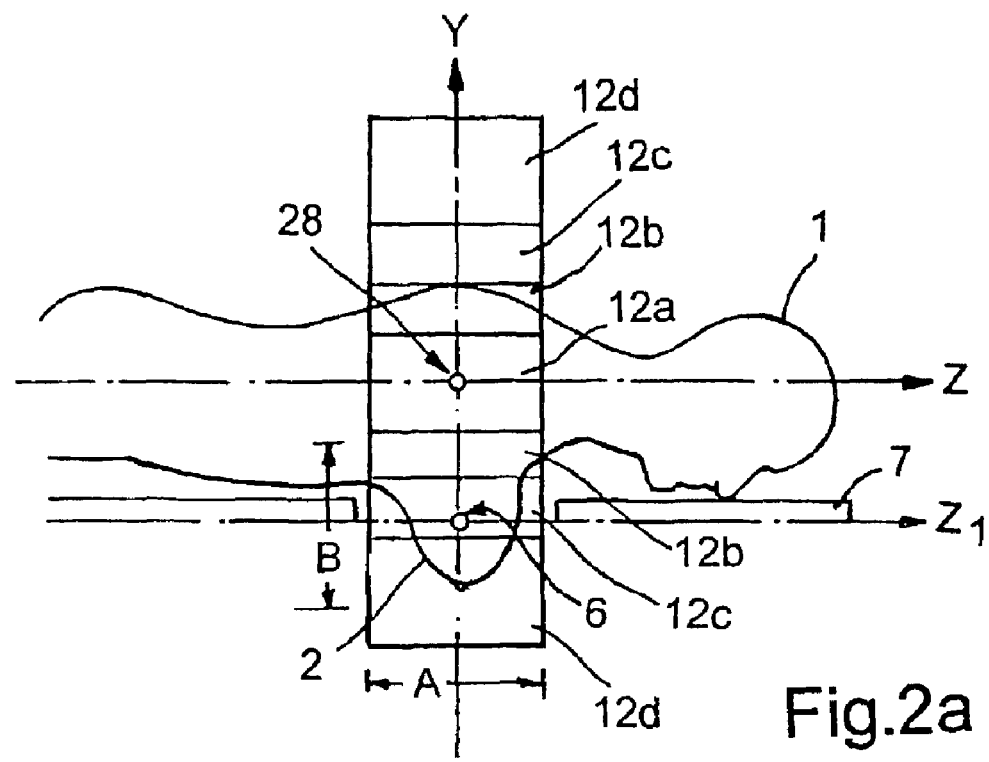
FIG. 2a is a schematic lateral view of the patient drawn to illustrate the zones of varying degrees of homogeneity which is present within the bore of the magnet assembly.
Figure 2B:
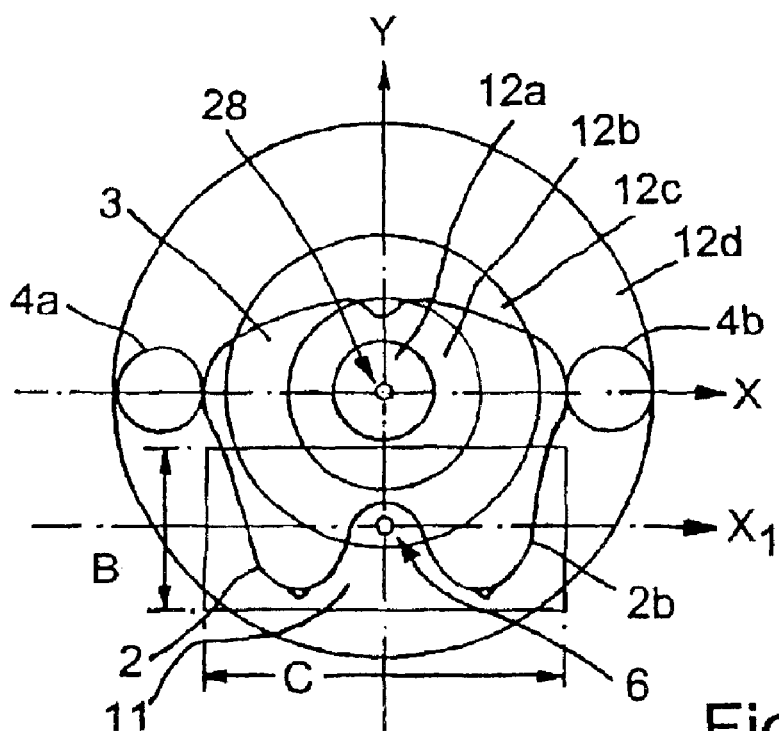
FIG. 2b is a schematic cross-sectional view of the patient drawn to illustrate the zones of varying degrees of homogeneity which is present within the bore of the magnet assembly.
Figure 3A:
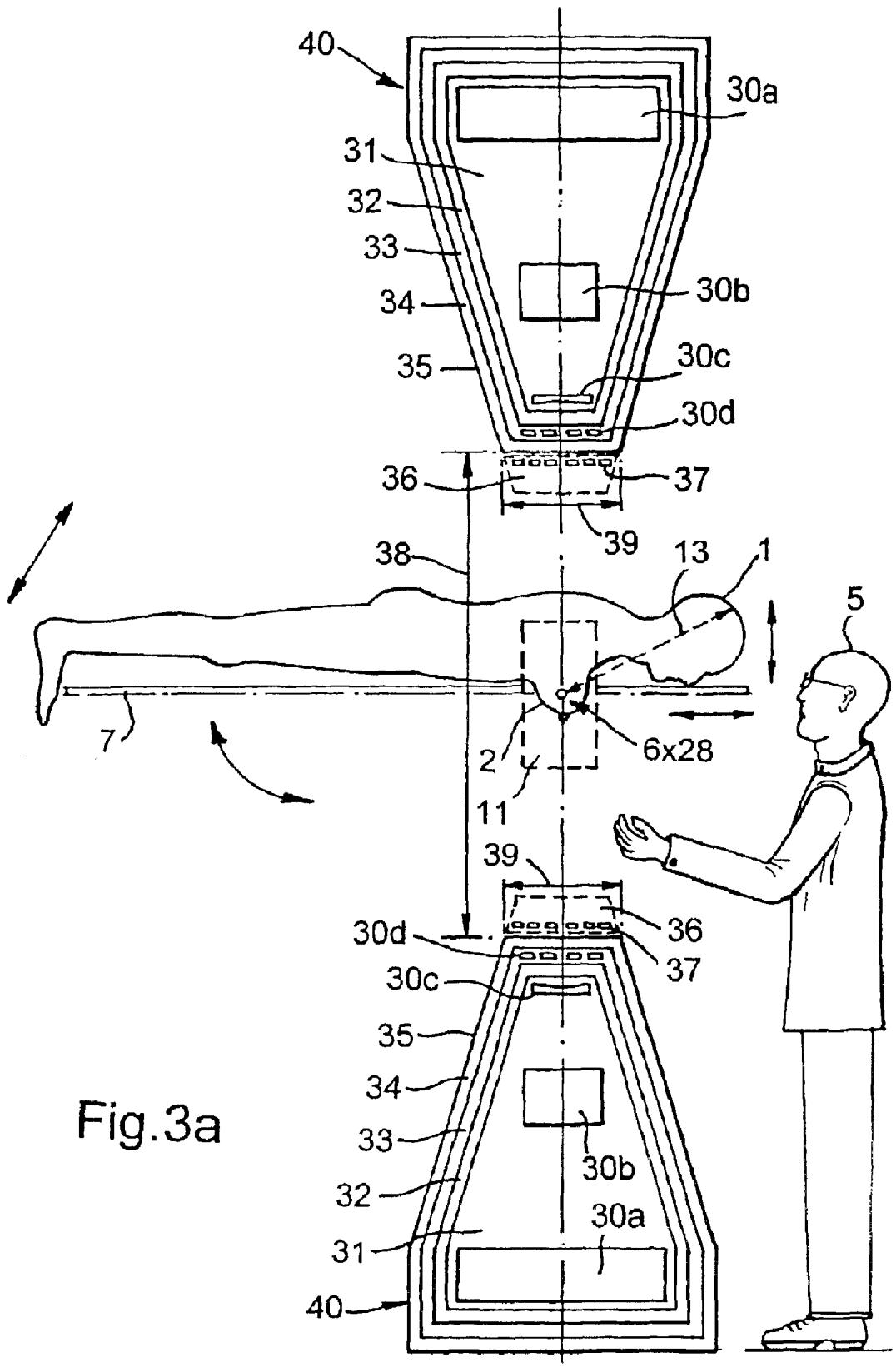
FIG. 3a is a schematic longitudinal section of an embodiment of the present invention for use with a patient in the prone position.
Figure 3B:
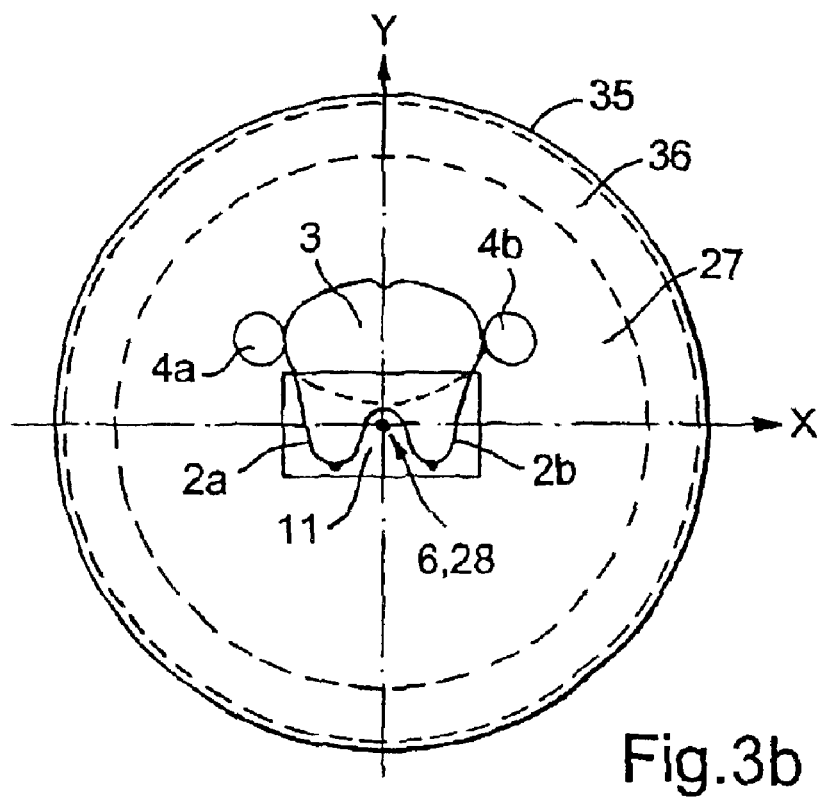
FIG. 3b is a schematic cross sectional view of the embodiment of FIG. 3a in which the centre of the anatomy-of-interest which comprises the two breasts of the patient is arranged coincident with the geometrical centre of the magnet.
Figure 3C:
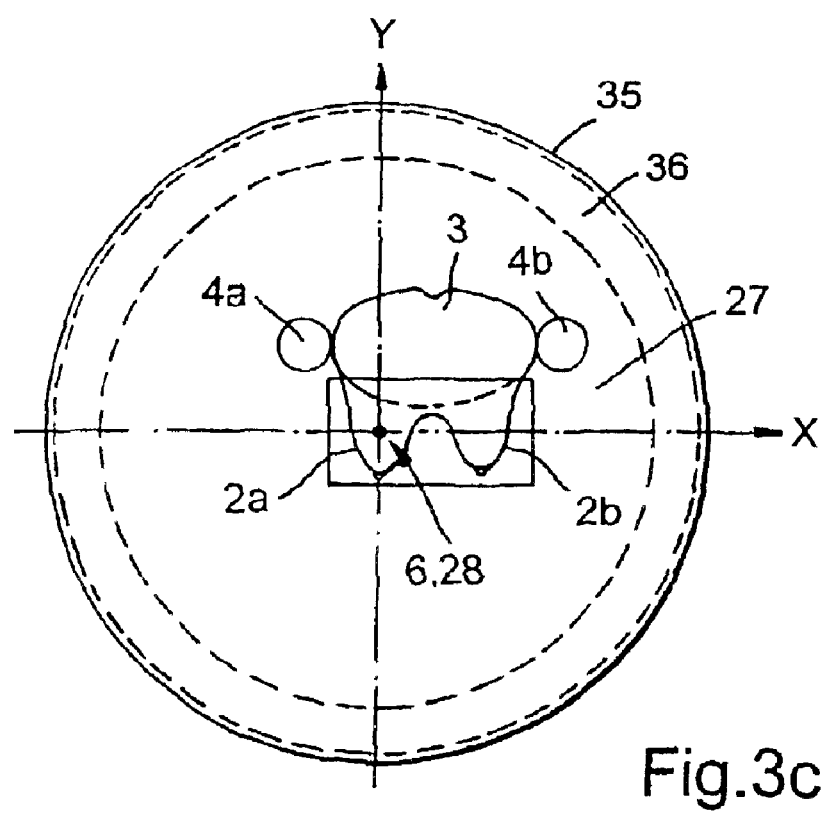
FIG. 3c is a schematic cross sectional diagram of the embodiment of FIG. 3a in which the centre of the anatomy-of-interest comprising single breast of the patient is arranged coincident with the geometrical centre of the magnet assembly.

Referring to FIGS. 3a, 3b and 3c, a magnet assembly 40 with four groups of coils is illustrated. As it will be appreciated the size and complexity of the magnet assembly 40 in terms of number of conductors will very much be dependent on the specification (size, location) of the 'imaging-field-zone' 11. The magnet assembly of FIGS. 3a, 3b and 3c comprises firstly a group of 'primary-coil(s)' 30a situated about the imaging-field-zone 11 which generate the main bulk of the static magnetic field over the anatomy-of-interest (e.g. breast (2)). The coils within the primary-coils group are made low-temperature (~4°K–10°K/liquid helium) super conductor material such as Niobium Titanium (NbTi) or Niobium Tin ($Nb_3S_n$). This assembly may also comprise a second group of 'coarse-correction-coil(s)' 30b which are positioned coaxially within the primary-coil(s) 30a and some or all may carry currents which flow in the opposite direction to the current carried by the primary-coil(s). The function of the 'coarse-correction' coil(s) 30b is to apply a first degree (coarse) correction/shimming on the field generated by the primary-coil(s). Again the 'coarse-correction coil(s)' 30b are made of low-temperature superconductive materials. The third set of coils within this assembly are the 'fine-correction coil(s)' 30c. These coils are positioned much more closely to the 'imaging-field-zone' 11 and again disposed coaxially with respect to the primary 30a and coarse-correction coil 30b groups, and their function is to apply fine correction/shimming to the field within the imaging-field-zone 11. If the degree of field homogeneity is desired to be increased further, a forth set of 'finer-correction coil(s)' 30d may potentially be incorporated into assembly of the magnet. These 'finer-correction coil(s)' may be made of high-temperature (>70°K–80°K/liquid nitrogen) superconductive materials such as YBCO (Yttrium-Barium-Copper-Oxide) or BSCCO (Bismuth-Strontium-Calcium-Copper-Oxide) and may be disposed much more closely to the imaging-field-zone 11 by placing them within the liquid nitrogen chamber 33 of the cryostat in order to enhance their contribution to the finer correction process. And finally, there is the option of positioning 'finest-correction coil(s)' 37 within the bore of the magnet assembly which could take the form of using, this time, room temperature (RT) conductors made of copper (Cu) material. These last group of correction coils may be disposed even more closer to the imaging-field-zone 11 by placing them within the zone 36 allocated also for other subsystems (e.g. gradient-coil and radio-frequency antenna) of the MR scanner. The zone 36 is not inside the cryostat but outside the superconductive magnet assembly and therefore is room temperature.

The primary-coil group 30a, the coarse-correction-coil group 30b and the fine-correction-coil group 30c are arranged within a low temperature chamber 31 at ~4°K–10°K (i.e. liquid helium temperature range). Surrounding the low temperature chamber 31 is a thermal radiation shield 32 and surrounding the thermal radiation shield 32 is a high temperature chamber 33 at 70°K–80°K (i.e. liquid nitrogen temperature range). Surrounding the high temperature chamber 33 is a vacuum chamber 34 contained within an outer enclosure 35 which is exposed to ambient room temperature.

The magnet assembly 40 tapers in axial length radially towards the magnet axis on which the geometrical centre 28 of the magnet lies. This tapering improves access to the patient 1 lying along the axis on the patient positioner 7. The centre 6 of the anatomy-of-interest 2 is coincident with the geometrical centre 28 of the magnet. Thus, a healthcare professional 5 is able to easily access the anatomy-of-interest 2 of the patient 1 whilst it is positioned within the imaging-field-zone 11 of the magnet assembly.

In the bore of the magnet assembly 40, there is provided a region 36 for room temperature shim coils 37, gradient coils (not shown) and radio frequency coils (not shown) which are required as is well understood by a skilled person in the art of magnetic resonance imaging.

As can be seen in FIGS. 3*b* and 3*c*, in view of the large bore 27 of the magnet assembly 40, the patient can be manoeuvred laterally relative to the axis of the bore 27 within the bore 27 to place the centre 6 of the anatomy-of-interest 2 coincident with the geometrical centre 28 of the magnet. FIG. 3*a* also illustrates that the patient can be inclined in any direction to the axis. In FIG. 3*b*, the anatomy-of-interest comprises both breasts 2*a* and 2*b* whereas in FIG. 3*c* the anatomy-of-interest comprises a single breast 2*a*. In order to be able to place the centre of the anatomy-of-interest constant with the axis 28 and thus the centre 6 of the imaging-field-zone 11, the bore of the magnet must be substantially larger than anything available in the prior art. The reason for placing the centre of the anatomy of interest at the centre of the imaging field zone 11 is that the centre of the imaging field zone will have a homogeneity which is highest at its centre. The homogeneity gradually decreases moving away from the centre. Thus the highest fidelity images can be obtained by placing the centre of anatomy of interest at the centre of the imaging field zone. This selective positioning of the anatomy-of-interest to provide the highest fidelity images possible is not something which has been considered in the prior art.

Figure 4:
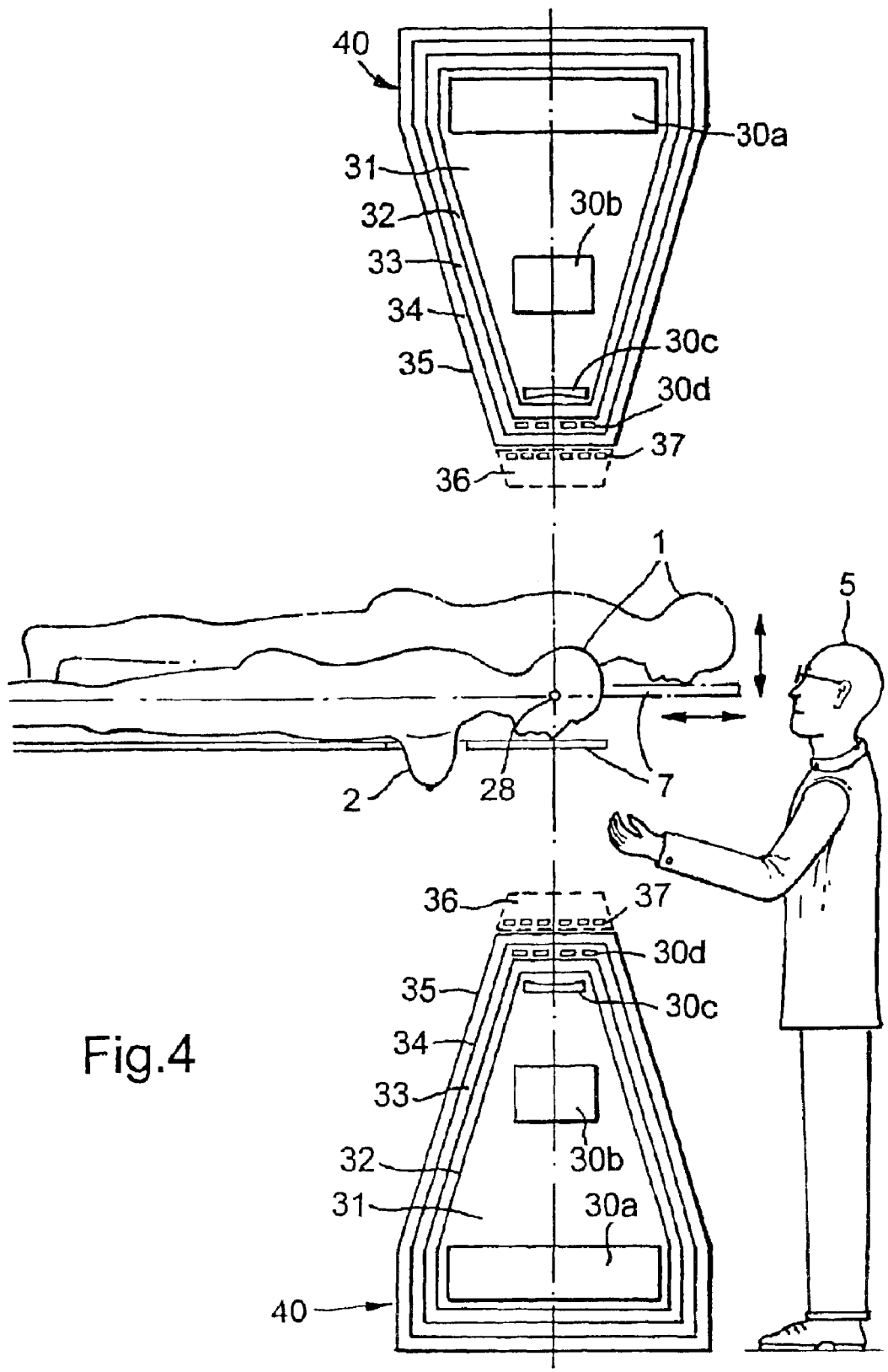
FIG. 4 is a schematic longitudinal sectional view of the first embodiment of the present invention illustrating the flexibility provided by the magnet assembly in being able to image different parts of the human anatomy.

FIG. 4 is an illustration of the arrangement of the first embodiment of the present invention illustrating the flexibility provided by the large bore magnet assembly. As can be seen in this figure, the patient 1 arranged on the patient-positioner 7 can be moved to position any part of the patient's anatomy at the geometrical centre 28 of the magnet. Thus in this example, the patient is moved from the position to image the breasts to a position to image the head. Whatever part of the patient's anatomy is placed at the geometrical centre for imaging, the large bore of the magnet enables the healthcare professional 5 to easily gain access to the anatomy-of-interest. In order to provide the relative movement between the magnet assembly 40 and the patient 1, it is possible to provide actuator means (e.g. hydraulic, pneumatic, electrical or mechanical) to move the patient on the patient positioner 7 within the bore of a fixed magnetic assembly 40. The means can comprise any suitable controlled actuator for moving the patient positioner 7. Alternatively, the patient positioner 7 could be held stationary and the magnet assembly 40 can be moved in three dimensions to be positioned such that its geometric centre is positioned at the centre of the anatomy-of-interest. The magnet assembly can be moved by any suitable controlled actuator to provide three axis control of the movement of the magnet assembly 40.

Figure 5:
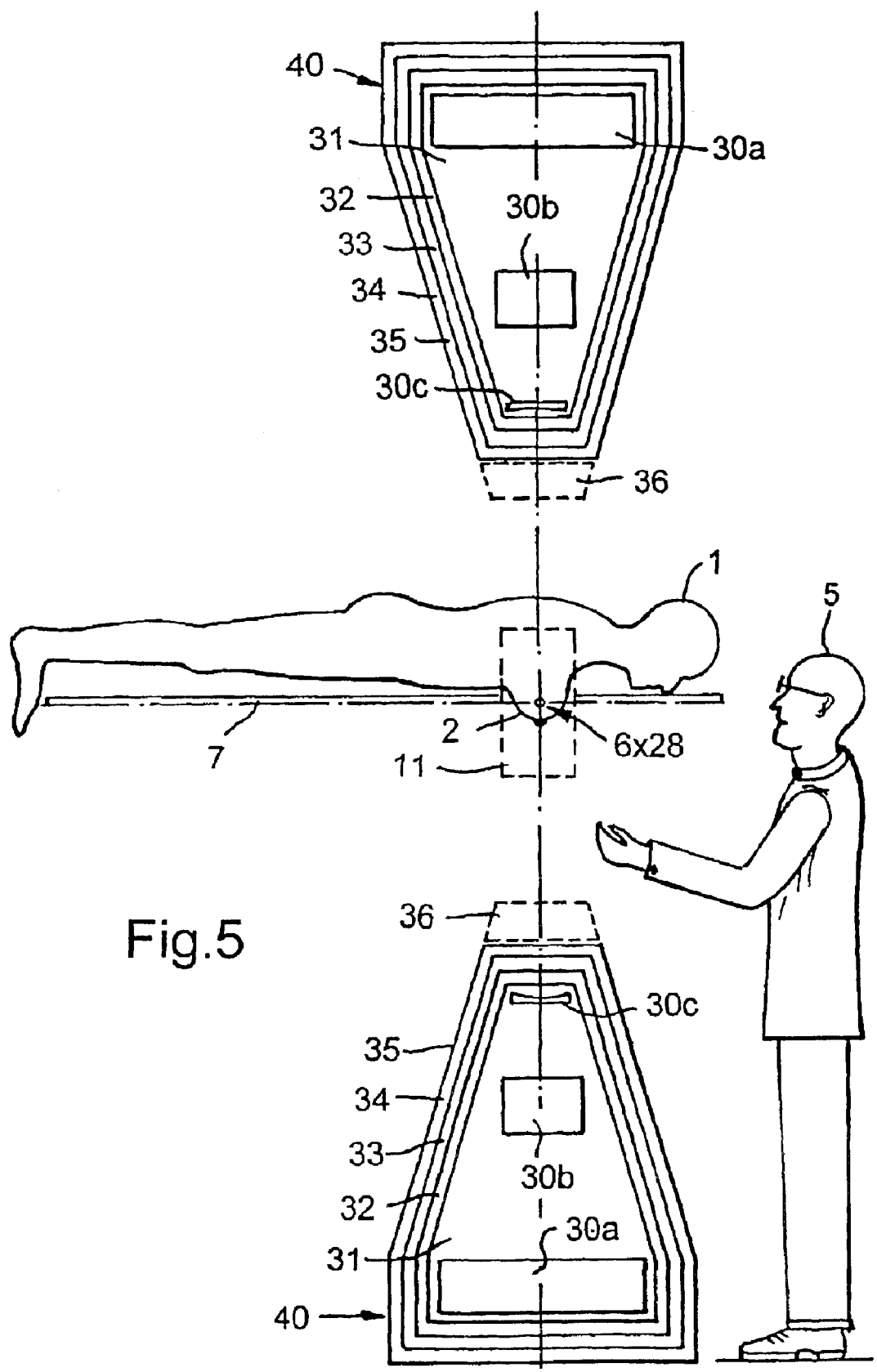
FIG. 5 is a schematic longitudinal sectional view of a second embodiment of the present invention.

FIG. 5 illustrates an alternative embodiment to the present invention in which the coil family 30 comprises only the primary-coil group 30*a*, the coarse-correction-coil group 30*b* and a single fine-correction-coil group 30*c* all formed of low temperature superconductive material and arranged within the low temperature chamber 31. This embodiment is otherwise similar to the first embodiment.

Figure 6:
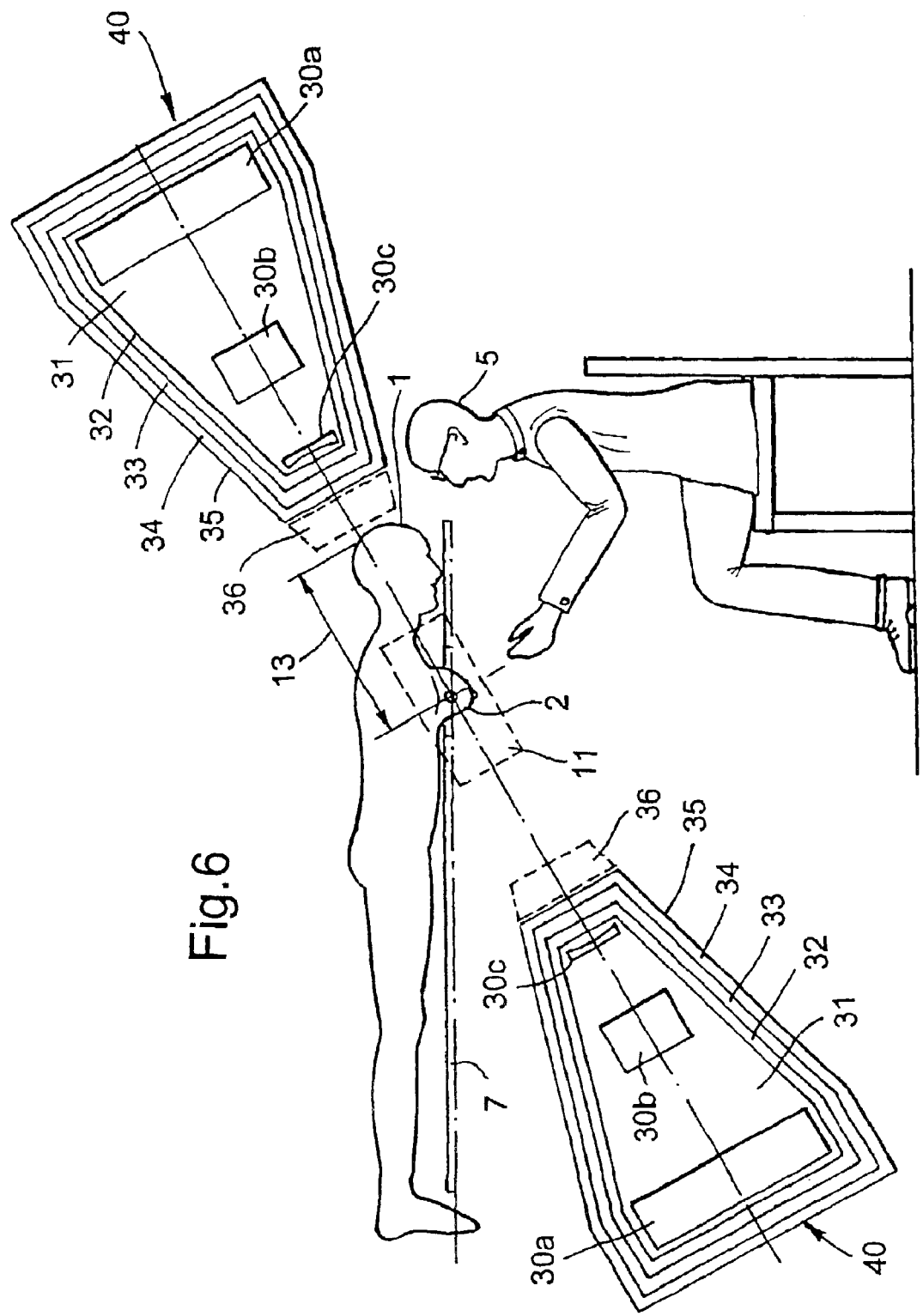
FIG. 6 is a longitudinal sectional view of a third embodiment of the present invention in which the magnet assembly is inclined relative to the patient.

FIG. 6 illustrates a third embodiment of the present invention in which the patient 1 is positioned in a prone position on the patient-positioner 7 as in the first and second embodiments. However, in this embodiment, magnet assembly of the second embodiment is used at an inclined angle to the patient 1 rather than being vertical. This configuration permits an even more open access to the patient 1 for the healthcare professional 5. As in the first and second embodiments, the patient 1 is positioned in the prone position which is a preferred posture during breast MR imaging. As can be seen in FIG. 6, the diameter of the bore of the magnet assembly 40 is sufficiently enlarged that it enables the breast of a patient to be positioned on the axis whilst the patient is rotated at relatively large angles. In order to accomplish this the bore has a radius greater than the distance 13 between the iso-centre of the breast 2 of the patient 1 and the tip of her head. As can be seen in FIG. 6, this enables the patient to be pivoted about the isocentre of the breast to maintain the breast at the centre of the imaging field zone 11 of the magnet assembly 40.

Figure 7:
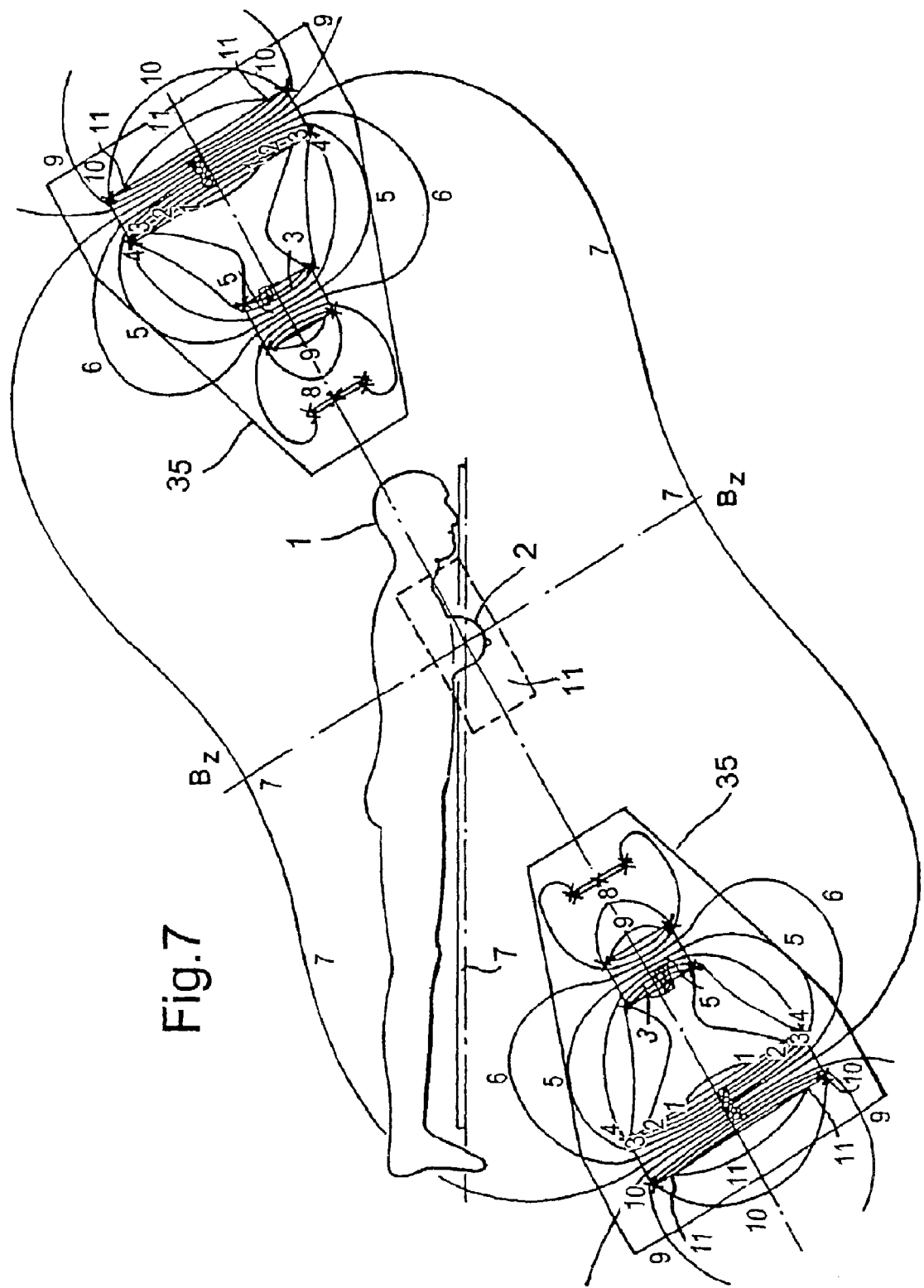
FIG. 7 is a schematic longitudinal view of the embodiment of FIG. 6 illustrating typical contour plots of the $B_z$ component of the magnetic field flux density vector $B(x,y,z)$.

FIG. 7 illustrates schematically typical contour plots of $B_z$ component of the magnetic flux density vector $B(x,y,z)$ for the arrangement of FIG. 6.

Figure 8:
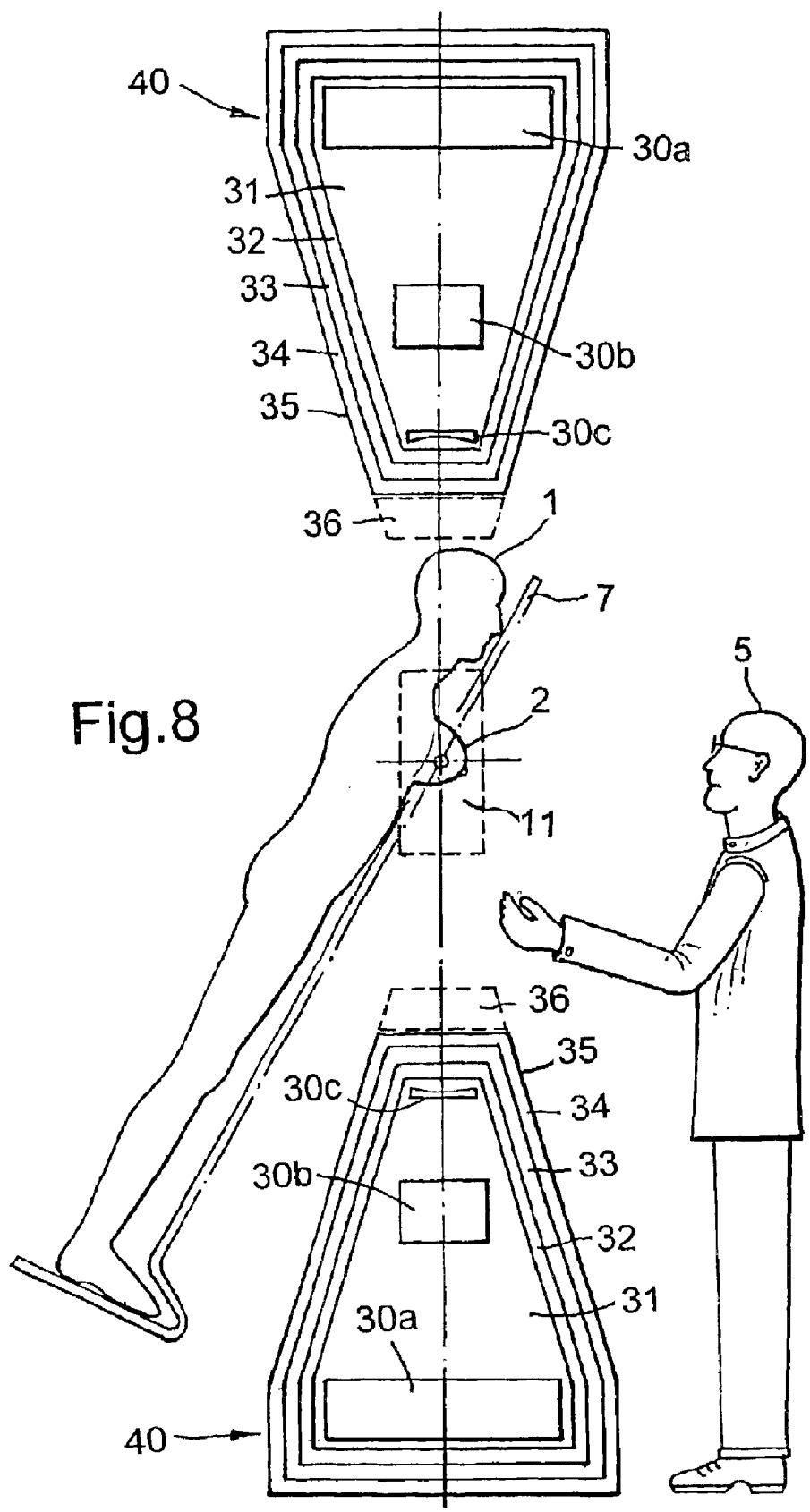
FIG. 8 is a schematic longitudinal sectional view of a fourth embodiment of the present invention in which the magnet assembly is arranged vertically and the patient is inclined relative thereto.

FIG. 8 illustrates a fourth embodiment of the present invention which uses the same magnet assembly as in the second and third embodiments. The magnet assembly is arranged vertically as in the second embodiment but in this embodiment the patient 1 is arranged inclined on a patient-positioner 7 in a semi-erect posture. This posture is also a preferred posture in breast MR imaging. It can clearly be seen from this that the healthcare professional 5 is provided with free and easy access to the breasts being imaged.

Figure 9:
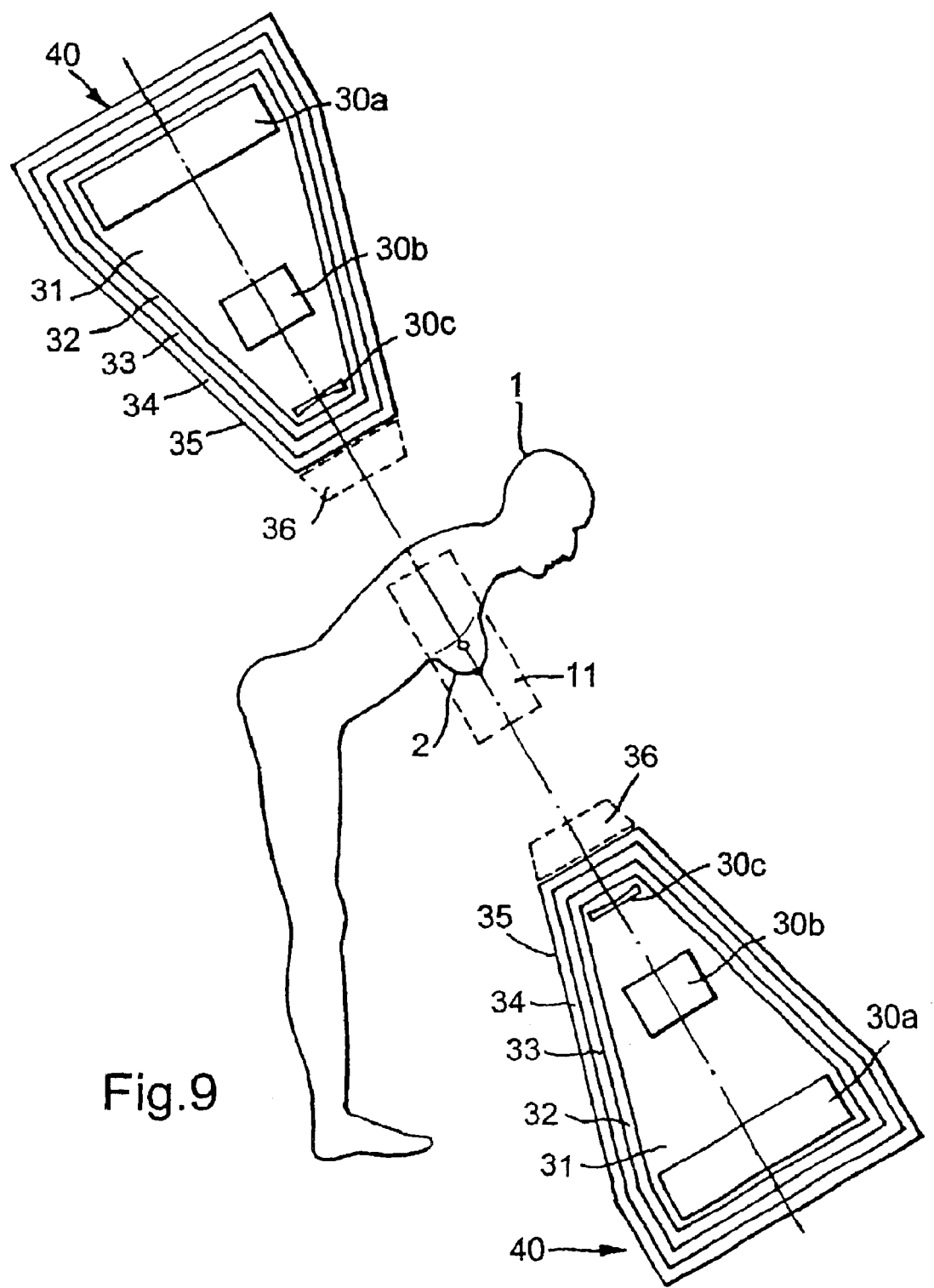
FIG. 9 is a schematic longitudinal sectional view of a fifth embodiment of the present invention in which the magnet assembly is tilted and the patient is arranged in a semi-erect posture.

Referring now to FIG. 9, which illustrates a fifth embodiment of the present invention, in this arrangement the magnet assembly comprises the same magnet assembly 40 as described for the second, third and fourth embodiments of the present invention. The magnet assembly 40 is tilted and the patient 1 is positioned bent over in a semi-erect posture.

Figure 10:
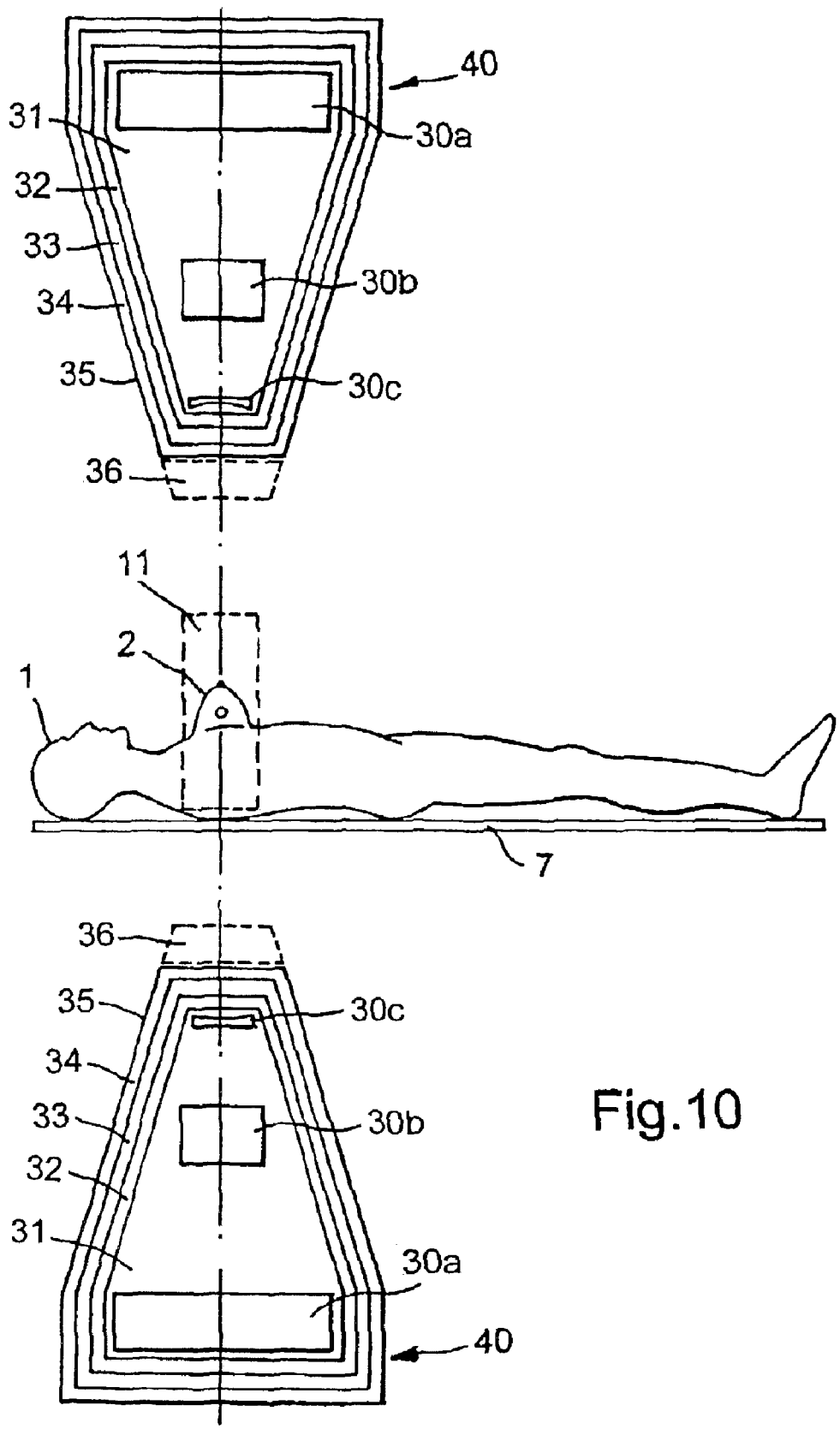
FIG. 10 is a schematic longitudinal sectional view of a sixth embodiment of the present invention in which the patient is positioned in the bore of the magnet assembly on their back (supine position)

FIG. 10 illustrates a sixth embodiment of the present invention similar to the second embodiment of the present invention except that the patient 1 is in a supine position.

FIG. 11 illustrates a seventh embodiment of the present invention in which the magnet assembly 400 has a rectangular cross section rather than the tapered cross section of the previous embodiments. Otherwise the general structure of the magnet assembly is the same. The magnet assembly comprises a superconductive coil family 300 comprising a primary-coil group 300*a*, a coarse-correction-coil group 300*b* and a fine-correction-coil group 300*c* arranged in a low temperature chamber 310 which is surrounded by a thermal radiation shield 320. The thermal radiation shield 320 is surrounded by a high temperature chamber 330 which is in turn surrounded by a vacuum chamber 340. The vacuum chamber 340 is enclosed within an enclosure 350 which is exposed to ambient room temperature. Radially inwards of the superconductive coil family 300 there is provided a region 360 for the room temperature shim coils (not shown) gradient-coils (not shown) and radio frequency coils (not shown).

As can be seen in FIG. 11, even with a magnet assembly 400 of rectangular cross section, because of the short axial length of the magnet assembly, the healthcare professional 5 is able to gain easy access to the anatomy-of-interest 2. This is particularly so when the magnet assembly and the patient are relatively inclined.

Figure 12A:
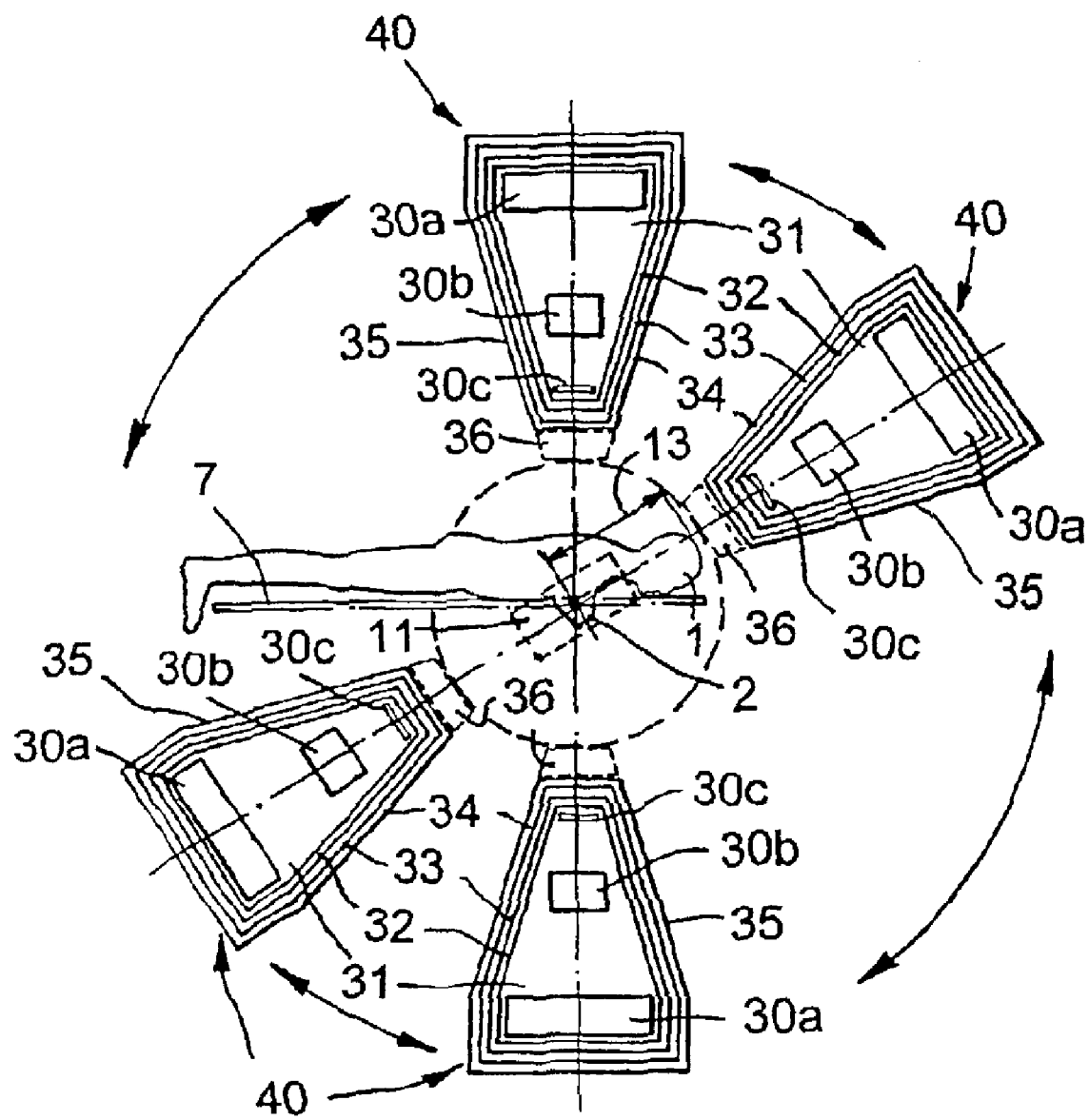
FIG. 12a is a diagram illustrating a method of rotating the magnet assembly of the embodiment of FIG. 6 to enable the imaging plane to be selected.

FIG. 12*a* illustrates a method of relatively inclining the patient and the magnetic assembly of the third embodiment of the present invention. Within the bore the imaging-field-zone is disk shaped and centred on the geometric centre of the magnet assembly. It can be seen from FIG. 12a that any anatomy of interest can be positioned at the centre of the imaging-field-zone in the region of highest homogeneity and the position and relative direction of the image plane in the anatomy of interest can be selected by the relative inclination of the patient and the magnet assembly. This enables a healthcare professional to select the image plane. As can be seen in FIG. 12a, the imaging field zone 11 extends more radially than axially within the bore. The homogeneity within the imaging field zone gradually decreases across the imaging field zone and because the radial length is greater than the axial length of the imaging field zone, the region of high homogeneity is greater in the radial direction than in the axial direction. Therefore the homogeneity within a trans-axial (transverse) plane tend to be relatively better than other imaging planes (e.g. sagital-plane, coronal-plane or an oblique plane) within the imaging-field-zone. Thus a healthcare professional can select and make use of the imaging plane with the highest homogeneity (e.g. transverse-plane) and as a result obtain an image of the anatomy-of-interest with even more improved fidelity.

Figure 12B:
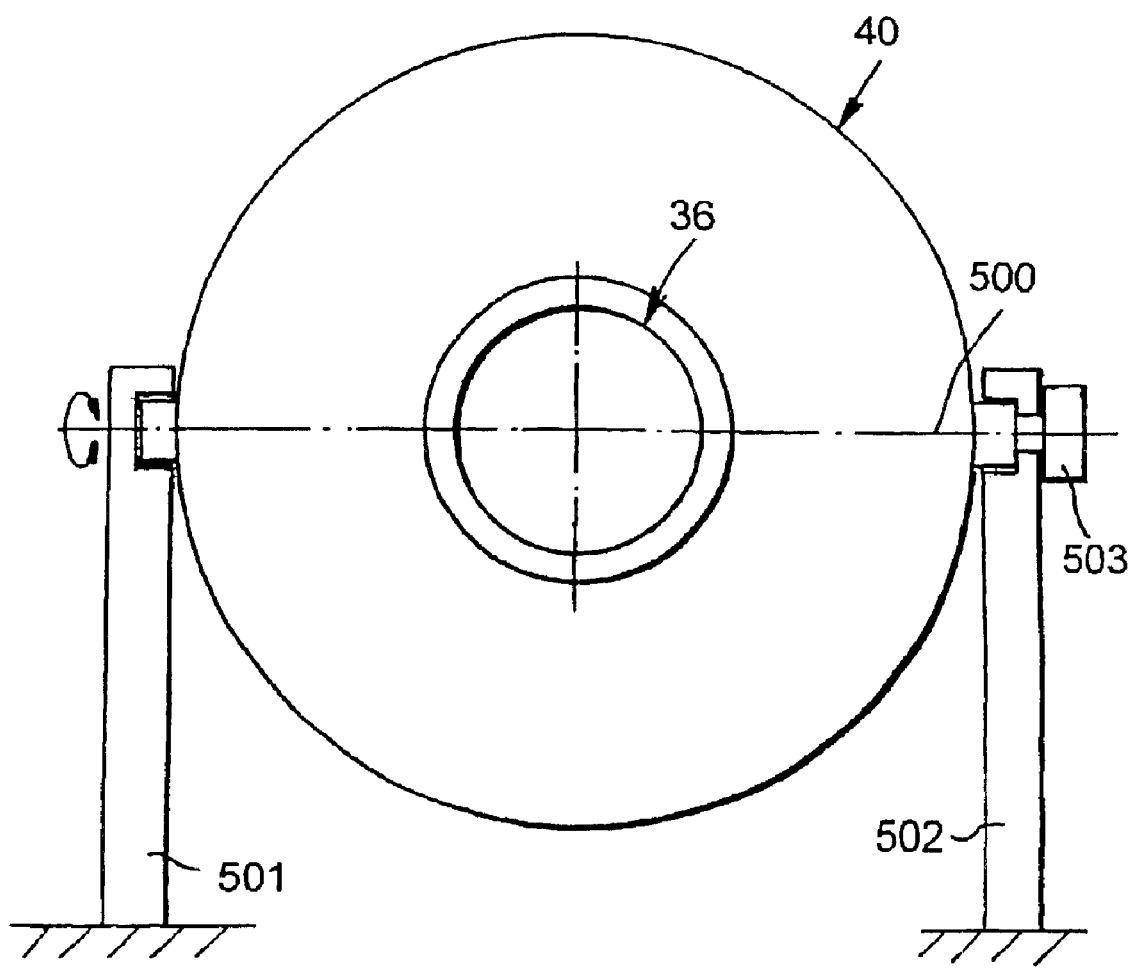

FIG. 12b illustrates an arrangement for achieving the rotation of the magnet assembly 40 about a pivot axis 500 coincident with the centre of the imaging field zone of the magnet assembly 40. As can be seen in FIG. 12b, the means to rotate the magnet comprises two pivotal support members 501 and 502 and an actuator 503. Any suitable actuator can be used to rotate the magnet assembly 40 in the pivot support members 501 and 502.

Figure 13:
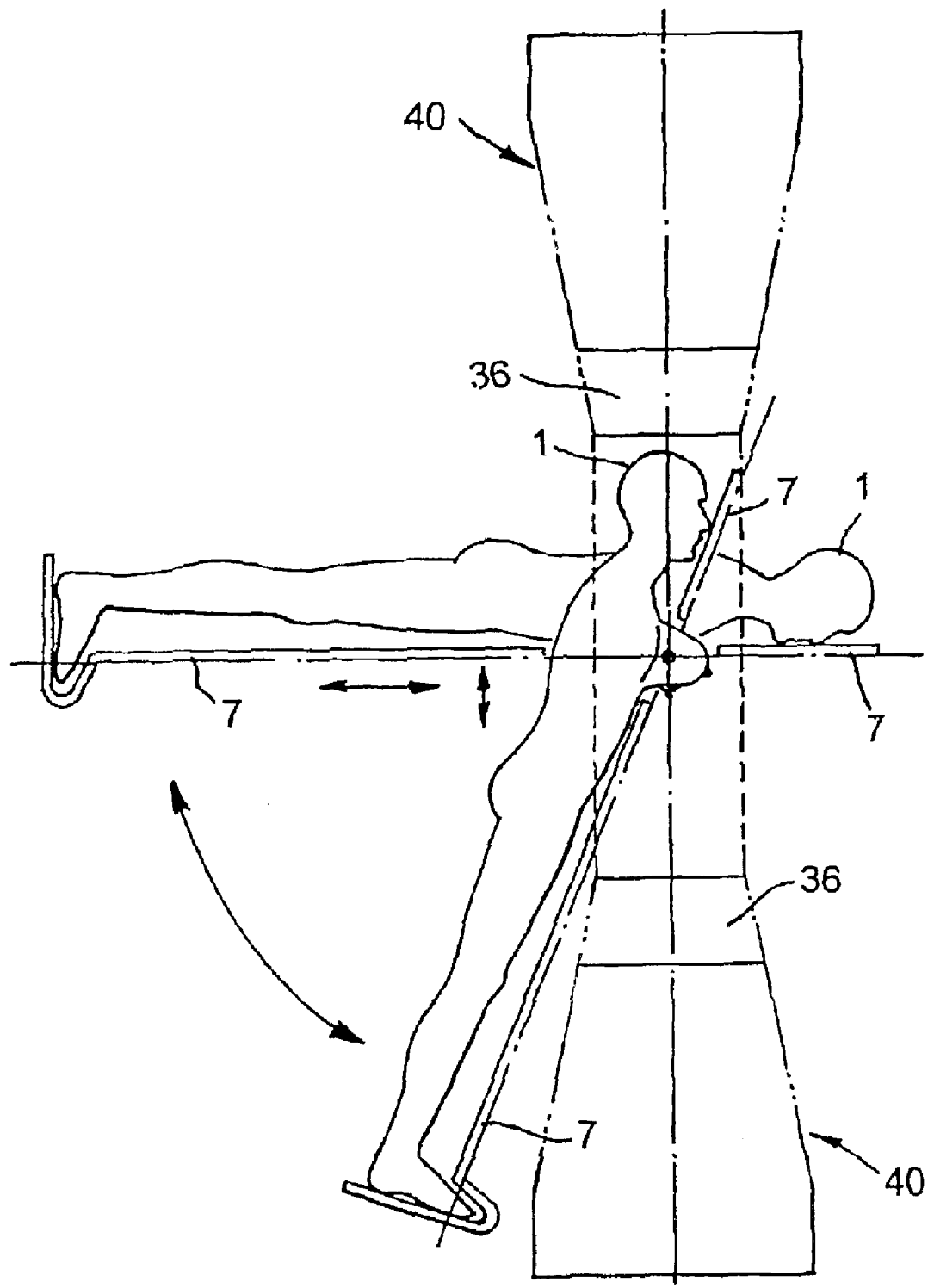
FIG. 13 is a diagram illustrating an alternative method of relatively inclining the patient and the magnet assembly by rotating the patient within the bore of the magnet assembly.

FIG. 13 illustrates alternative method of achieving the relative rotation of the patient 1 and the magnetic assembly 40. In this embodiment the patient is held on a patient positioner 7 and the patient positioner 7 is mounted so as to be relatively rotatable within the bore. The patient positioner 7 can be held by a suitable support and driven by any suitable actuator under control of any suitable control means. As can be seen in FIG. 13 the relative rotation is preferably capable of maintaining any anatomy of interest of the patient at the geometric centre of the magnet assembly 40. This can be achieved by allowing the three dimensional movement of the patient positioner 7 within the bore and the relatively rotation of the patient positioner 7 in the bore. A suitable array of actuators and associated controllers can be used to achieve this movement of the patient positioner 7.

In both the embodiments of FIGS. 12a, 12b and 13, the patient and the magnet assembly can be relatively positioned about the axis of the bore or relatively inclined to the axis prior to the patient being inserted in the bore i.e. before the relative movement of the magnet assembly and the patient along the axis of the bore. Alternatively, the relative positioning can take place once the patient is in the bore. In the embodiments illustrated hereinabove, the diameter 38 of the bore is sufficiently large to receive a patient 1 within the bore and to allow for the positioning of any part of the patient to be imaged on the axis on the centre 28 of the bore. In one embodiment of the present invention, the bore of the magnet has a diameter 38 larger than twice the length 13 measure between the centre 6 of the breast of a female with an average height and the tip of her head. Accordingly, in the preferred embodiment the diameter 38 of the bore is at least 110 cm. The axial length 39 of the bore is a maximum of 40 cm. The overall outer diameter (not shown) of the magnet assembly is in the region of 2.0 to 2.5 meters. It can thus be seen that although the magnet assembly is radially large, axially it is short. The use of large radial dimensions ensures that a large bore can be provided in order to provide for a flexible MR imaging system which can image any part of the body whilst allowing access to that part of the body by healthcare professionals 5.

It can be seen from the foregoing embodiments that the large bore and axially short magnet assembly permits the preferred positioning of the anatomy-of-interest. For example, there is a general consensus within the healthcare profession that imaging of the female breast is carried out when the patient is in a prone position where the female breast hangs naturally under gravity. The semi-erect position is also a preferred posture for the same reason and also a comfortable posture for the patient. It can be seen from the foregoing embodiments that such postures are provided for whilst maintaining the anatomy-of-interest within the most homogenous region of the magnetic field.

It would also be apparent from the foregoing embodiments that the large bore magnet allows totally free access to the patient by healthcare professionals during imaging. Access to the patient is highly desirable for the purposes of performing;

(a) interventional diagnostic procedures e.g. a fine needle biopsy, or core biopsy under MR imaging guidance i.e. the procedure is carried out whilst imaging in real-time or near real-time., (b) open surgical treatment procedures, e.g. lumpectomy, and (c) minimally invasive treatment procedures e.g. ablation or tumours using localised laser, radio frequency energy and focused ultrasound energy.

The large bore and axially short magnet assembly also permits the imaging of the anatomy-of-interest whilst under exercise. For example, it is highly desirable to be able to image and study the functions of the heart, cardiovascular system and skeletal system whilst the patient is exercising e.g. on a treadmill.

Figure 14:
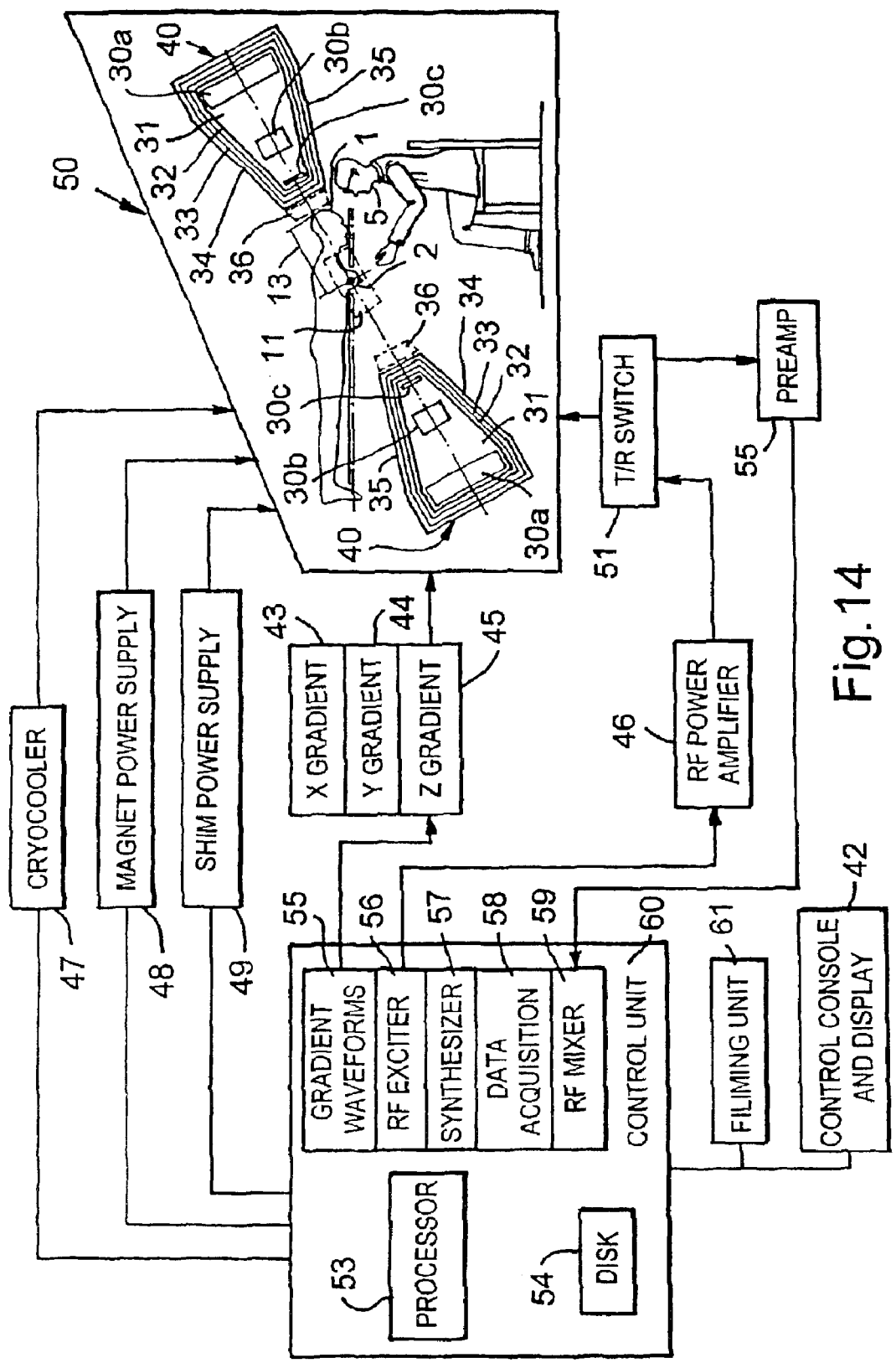
FIG. 14 is a schematic diagram of a MR imaging system of an embodiment of the present invention utilising the MR imaging magnet assembly.

An MR imaging system incorporating the magnet assembly 40 (or 400) in accordance with an embodiment of the present invention will now be described with reference to FIG. 14. The superconductive magnet assembly 40 together with the other subsystems of the MR imaging system housed in zone 36 (i.e. room temperature shim-coils 37, gradient coils (not shown) and RF coils (not shown)) will be referred to as 'MR Front-End' 50. Apart from the magnet assembly 40, the MR imaging system of FIG. 14 is of conventional form.

A magnet power supply 48 is provided for ramping the magnetic field of the magnet assembly 40 up (or down) by applying current to the coils of the magnet assembly. The shim power supply 49 adjusts the current within the room temperature shim coils 37 (also referred to as 'finest correction coils') thus adjusting the homogeneity of the magnet assembly. A cryocooler 47 is provided to cool the cryogenic fluids within the magnet to eliminate boil off of cyogenic fluids and the attendant costs. The shim power supply 49, the magnet power supply 48 and the cryocooler 47 are all under the control of a processor 53 within a control unit 60.

Gradient magnetic fields are generated by the X, Y and Z gradient coils (not shown but housed inside the zone 36 and forms part of the MR Front-End 50) which are driven by the X, Y and Z gradient amplifiers 43, 44 and 45. Gradient waveforms are generated by a gradient waveform circuit 55 which is part of the control unit 60.

RF waveforms are generated by a RF exciter 56 in conjunction with a frequency synthesiser 57. The RF waveforms are passed to a RF power amplifier 46 to be amplified. The amplified RF signals are passed through transmit/ receive (T/R)switch 51 to drive the RF coil (not shown but housed inside the zone 36 and forms part of the MR Front-End 50). Since the same RF coil may be used for both to transmit RF energy into the patient and to receive the magnetic resonance signal back from the patient, the provision of a T/R switch 51 is necessary. A low-noise preamplifier 52 is provided in order to amplify the magnetic resonance signals picked up by the RF coil when it is operating in 'receive-mode'. The signal amplified by the amplifier 52 is mixed by an RF mixer 59 within the control unit 60 to a frequency where it can be sampled in a data acquisition system 58 within the control unit 60 and converted into digital form for further processing by the processor 53.

The processor 53 orchestrates all the various sub-systems. Once data has been received back through the data acquisition system 58, the processor 53 uses, typically, a Fourier transform to reconstruct one or more cross sectional images of the patient. Images are stored on a disk 54 and may also be hard copied onto a filming unit 61. A control console and display 42 is provided to allow an operator to control the system while monitoring the patient. Images may also be displayed on the control console and display 42, both for diagnosis, and for the monitoring of image acquisition.

Although the present invention has been described hereinabove with reference to specific embodiments, it will be apparent to a skilled person in the art that modifications are possible within the spirit and scope of the present invention.

It would be apparent to a skilled person in the art of magnet design for MR imaging that, in order to control the extent of magnetic field generated by the magnet and prevent the fringing of the field beyond the boundaries of a given space (i.e. the room in which the magnet is sited), active and/or passive magnetic shielding methods can be used such as those described in GB 2285313, the content of which are hereby incorporated by reference.

It will also be apparent to a skilled person in the art of magnet design for magnetic resonance imaging that, in order to maintain the magnet of the current invention at low temperatures, in addition to the use of liquid helium and liquid nitrogen, one or more cryocoolers may be used, or the magnet of the present invention may be cooled purely by one or more cryocoolers without the use of any cryogenic fluids.

What is claimed is:

1. A magnetic resonance imaging method for taking an image of an anatomy of interest comprising part of a patient using a magnet assembly extending to form a bore into which the anatomy of interest of the patient can be placed, and having a plurality of coaxially-arranged coils surrounding the bore, the bore having a minimum diameter larger than the an axial length of the bore, the method comprising:

three dimensionally positioning the patient or said magnet assembly so that a center of the anatomy of interest of the patient is statically positioned at a center of an imaging-field-zone of the magnet assembly on an axis of said bore in said bore during imaging;

inducing current flow in said coils so as to produce a magnetic field in the imaging-field-zone, wherein the magnetic field has a homogeneity that is highest at the center of the imaging-field-zone and decreases moving away from the center;

forming gradient magnetic fields in the imaging-field-zone;

generating RF waveforms in the imaging-field-zone;

receiving a magnetic resonance signal from the anatomy of interest of the patient in the imaging-field-zone; and processing the signal to generate an image of the anatomy of interest of the patient.

2. A magnetic resonance imaging method according to claim 1, wherein a radius of the bore is greater than the a distance from the tip of the head of a human female of average height to the center of the breast of the human female of average height.

3. A magnetic resonance imaging method according to claim 1, including:

three dimensionally moving a patient or said magnet assembly so that a center of a second anatomy of interest of the patient that is to be imaged is statically positioned at the center of the imaging-field-zone of the magnet assembly;

inducing current flow in said coils so as to produce said magnetic field in the imaging-field-zone within said bore;

forming gradient magnetic fields in the imaging-field-zone;

generating RF waveforms in the imaging-field-zone;

receiving a magnetic resonance signal from the anatomy of interest of the patient in the imaging-field-zone; and processing the signal to generate an image of the second anatomy of interest of the patient.

4. A magnetic resonance imaging method according to claim 1, further including rotating the patient or said magnet assembly about a pivot point on the axis of the bore to maintain the anatomy of interest of the patient in the imaging-field-zone of the magnet assembly and to allow an image to be taken at a desired inclination;

inducing current flow in said coils so as to produce a homogeneous magnetic field in the imaging-field-zone within said bore;

forming gradient magnetic fields in the imaging-field-zone;

generating RF waveforms in the imaging-field-zone;

receiving a magnetic resonance signal from the anatomy of interest of the patient in the imaging-field-zone; and processing the signal to generate a second image of the anatomy of interest of the patient at the desired inclination.

5. A magnetic resonance imaging method using a magnet assembly having a bore into which an anatomy of interest of a patient can be placed, and a plurality of coaxially-arranged coils surrounding the bore, wherein a minimum diameter of the bore is at least 110 cm which is substantially larger than an axial length of the bore, the method comprising:

three dimensionally positioning the patient or said magnet assembly so that the anatomy of interest of the patient that is to be imaged is statically positioned at the center of an imaging-field-zone of the magnet assembly imaging;

inducing current flow in said coils so as to produce a substantially homogeneous magnetic field in the imaging-field-zone substantially on an axis of said bore to allow imaging of the whole anatomy of interest in the imaging-field-zone;

forming gradient magnetic fields in the imaging-field-zone;

receiving a magnetic resonance signal from the anatomy of interest of the patient in the imaging-field-zone; and processing the signal to generate an image of the anatomy of interest of the patient.

6. A magnetic resonance imaging method using a magnet assembly having a bore into which an anatomy of interest of a patient can be placed, and a plurality of coaxially-arranged coils surrounding the bore, wherein an axial length of said bore is less than 40 cm, the bore having a minimum diameter substantially larger than the axial length of the bore, the method comprising:

three dimensionally positioning a patient or said magnet assembly so that the anatomy of interest of the patient that is to be imaged is statically positioned at a center of an imaging-field-zone of the magnet assembly during imaging;

inducing current flow in said coils so as to produce a substantially homogeneous magnetic field in the imaging-field-zone substantially on an axis of said bore to allow imaging of the whole anatomy of interest in the imaging-field-zone;

forming gradient magnetic fields in the imaging-field-zone;

receiving a magnetic resonance signal from the anatomy of interest of the patient in the imaging-fleld-zone; and processing the signal to generate an image of the anatomy of interest of the patient.

7. A magnetic resonance imaging apparatus for taking an image of an anatomy of interest comprising part of a patient the apparatus comprising:

a magnet assembly extending to form a bore into which the anatomy of interest of the patient can be placed, and having a plurality of coaxially arranged coils surrounding the bore, the bore having a minimum diameter larger than an axial length of the bore;

positioning means for three dimensionally positioning the patient or said magnet assembly so that a center of the anatomy of interest of the patient is statically positioned at the center of an imaging-field-zone of the magnet assembly on the axis of said bore in said bore during imaging;

current means for inducing current flow in said coils so as to produce a magnetic field in the imaging-field-zone to allow imaging of the whole anatomy of interest in the imaging-field-zone, the magnetic field having a homogeneity that is highest at the center of the imaging-field-zone and decreases away from the center;

magnetic gradient means for forming gradient magnetic fields in the imaging-field-zone;

RF generating means for generating RF waveforms in the imaging-field-zone;

receiving means for receiving a magnetic resonance signal from the anatomy of interest of the patient in the imaging-field-zone; and processing means for processing the received signal to generate an image of the anatomy of interest of the patient.

8. A magnetic resonance imaging apparatus according to claim 7, wherein a radius of the bore is greater than a distance from the tip of the head of a human female of average height to the center of the breast of the human female of average height.

9. A magnetic resonance imaging apparatus according to claim 7, wherein said positioning means is adapted to three dimensionally move a patient or said magnet assembly so that a center of a second anatomy of interest of the patient that is to be imaged is positioned at the center of the imaging-field-zone of the magnet assembly; said receiving means is adapted to receive a magnetic resonance signal from the second anatomy of interest of the patient in the imaging-field-zone; and said processing means is adapted to process the received signal to generate an image of the second anatomy of interest in the patient.

10. A magnetic resonance imaging apparatus according to claim 7, further including rotating means for rotating the patient or said magnet assembly about a pivot point on the axis of the bore to maintain the anatomy of interest of the patient in the imaging-field-zone of the magnet assembly and to allow an image to be taken at a desired inclination;

wherein said receiving means is adapted to receive a magnetic resonance signal from the anatomy of interest of the patient in the imaging-field-zone at the desired inclination; and said processing means is adapted to process the received signal to generate an image of the anatomy of interest of the patient.

11. A magnetic resonance imaging apparatus, comprising:

a magnet assembly having a bore into which an anatomy of interest of a patient can be placed, and a plurality of coaxially arranged coils surrounding the bore, wherein a minimum diameter of the bore is at least 110 cm which is substantially larger than an axial length of the bore;

positioning means for three dimensionally positioning the patient or said magnet assembly so that the anatomy of interest of the patient that is to be imaged is statically positioned at the center of an imaging-field-zone of the magnet assembly;

current means for inducing current flow in said coils so as to produce a substantially homogeneous magnetic field in the imaging-field-zone substantially on the axis of said bore to allow imaging of the whole of the anatomy of interest in the imaging-field-zone;

magnetic gradient means for forming gradient magnetic fields in the imaging-field-zone;

RF generating means for generadting RF waveforms in the imaging-field-zone;

receiving means for receiving a magnetic resonance signal from the anatomy of interest of the patient in the imaging-field-zone; and processing means for processing the received signal to generate an image of the anatomy of interest of the patient.

12. A magnetic resonance imaging apparatus comprising:

a magnet assembly having a bore into which an anatomy of interest of a patient can be placed, and a plurality of coaxially arranged coils surrounding the bore, wherein an axial length of said bore is less than 40 cm, the bore having a minimum diameter substantially larger than the axial length of the bore;

positioning means for three dimensionally positioning the patient or said magnet assembly so that the anatomy of interest of the patient that is to be imaged is statically positioned at the center of an imaging-field-zone of the magnet assembly during imaging;

current means for inducing current flow in said coils so as to produce a substantially homogeneous magnetic field in the imaging-field-zone substantially on the axis of said bore to allow imaging of the whole of the anatomy of interest in the imaging-field-zone;

magnetic gradient means for forming gradient n-magnetic fields in the imaging-field-zone;

RF generating means for generating RF waveforms in the imaging-field-zone;

receiving means for receiving a magnetic resonance signal from the anatomy of interest of the patient in the imaging-field-zone; and processing means for processing the received signal to generate an image of the anatomy of interest of the patient.

13. A magnet assembly for use in a magnetic resonance imaging system for producing a magnetic resonance image of an anatomy of interest comprising part of a patient, the assembly comprising:

a bore into which the anatomy of interest of the patient can be placed; and a plurality of coaxially arranged coils surrounding said bore;

wherein said coils are arranged to generate a homogeneous magnetic field in an imaging-field-zone in said bore, the imaging-field-zone is larger than the anatomy of interest, and said bore has a minimum diameter of at least 110 cm which is larger than an axial length of said bore.

14. A magnet assembly according to claim 13, wherein the imaging-field-zone of the magnet assembly is on the axis of said bore.

15. A magnet assembly according to claim 13, wherein a radius of the bore is greater than a distance from the tip of the head of a human female of average height to the center of the breast of the human female of average height.

16. A magnet assembly for use in a magnetic resonance imaging system for producing a magnetic resonance image of an anatomy of interest of a patient, the assembly comprising:

a bore into which the anatomy of interest of the patient can be placed, wherein an axial length of said bore is less than 40 cm; and a plurality of coaxially arranged coils surrounding said bore;

wherein said coils are arranged to generate a substantially homogeneous magnetic field in an imaging-field-zone in said bore, the imaging-field-zone is larger than the anatomy of interest, and said bore has a minimum diameter substantially larger than the axial length of said bore and large enough to allow any anatomy of interest of the patient to be imaged to be positioned on the axis of said coils in said imaging-field-zone.

17. A magnet assembly for use in an magnetic resonance imaging system for producing a magnetic resonance image of an anatomy of interest comprising part of a patient, the assembly comprising:

a primary coil arranged about an axis for generating a primary magnetic field in an imaging-field-zone centered on said axis;

a correction coil arranged about said axis nearer said imaging-field-zone and coaxial with said primary coil means to generate a correction magnetic field in said imaging-field-zone which in combination with said primary magnetic field provides a substantially homogeneous magnetic field in said imaging-field-zone; and a housing for said primary coil and said correction coil, an inner wall of said housing defining a bore into which the anatomy of interest of the patient can be placed in said imaging-field-zone, said bore having a minimum diameter of at least 110 cm which is large enough to allow a center of any anatomy of interest of said patient to be placed on said axis and an axial length of less than the diameter.

18. A magnet assembly according to claim 17, wherein a radius of the bore is greater than a distance from the tip of the head of a human female of average height to the center of the breast of the human female of average height.

19. A magnet assembly for use in an magnetic resonance imaging system for producing a magnetic resonance image of an anatomy of interest of a patient, the assembly comprising:

a primary coil means arranged about an axis for generating a primary magnetic field in an imaging-field-zone centered on said axis;

a correction coil means arranged about said axis nearer said imaging-field-zone and coaxial with said primary coil means to generate a correction magnetic field in said imaging-field-zone which in combination with said primary magnetic field provides a substantially homogeneous magnetic field in said imaging-field-zone; and a housing for said primary coil means and said correction coil means, an inner wall of said housing defining a bore into which the anatomy of interest of the patient can be placed in said imaging-field-zone, said bore having a minimum diameter large enough to allow any anatomy of interest of said patient to be placed on said axis and an axial length of substantially less than the diameter, wherein the axial length of said bore is less than 40 cm.

20. A magnetic resonance imaging method for providing an image of an anatomy of interest comprising part of a patient using a magnet assembly extending to form a bore into which the anatomy of interest of the patient can be placed, and a plurality of coaxially arranged coils surrounding the bore, the bore having a minimum diameter larger than an axial length of the bore, the method comprising:

positioning a patient or said magnet assembly so that the patient is inclined relative to the axis of the magnet assembly and the anatomy of interest of the patient is positioned in an imaging-field-zone of the magnet assembly in said bore at a desired inclination to allow an image to be taken an the desired inclination;

inducing current flaw in said coils so as to produce a homogeneous magnetic field in the imaging-field-zone within said bore;

forming gradient magnetic fields in the imaging-field-zone;

generating RF waveforms in the imaging-field-zone;

receiving a magnetic resonance signal from the anatomy of interest of the patient in the imaging-field-zone; and processing the signal to generate an image of the anatomy of interest of the patient.

21. A magnetic resonance imaging method according to claim 20, wherein the positioning step comprises positioning the patient or said magnet assembly so that the patient is in said bore and rotating the patient or said magnet assembly about a pivot point on the axis of said bore to maintain the anatomy of interest of the patient in the imaging-field-zone of the magnet assembly and to allow an image to be taken in the desired inclination.

22. A magnetic resonance imaging method according to claim 20, further including;

rotating the patient or said magnetic assembly about said pivot point to maintain the anatomy of interest of the patient in the imaging-field-zone of the magnet assembly and to allow an image to be taken in a second desired inclination;

inducing current flow in said coils so as to produce a homogeneous magnetic field in the imaging-field-zone within said bore;

forming gradient magnetic fields in the imaging-field-zone;

generating RF waveforms in the imaging-field-zone;

receiving a magnetic resonance signal from the anatomy of interest of the patient in the imaging-field-zone; and processing the signal to generate a second image of the anatomy of interest of the patient.

23. A magnetic resonance imaging method according to claim 20, wherein the imaging-field-zone is on the axis of said bore.

24. A magnetic resonance imaging method according to claim 20, wherein said magnetic assembly has a reduced axial length nearer the axis of the bore.

25. A magnetic resonance imaging apparatus for providing an image of an anatomy of interest comprising part of a patient, the apparatus comprising:

a magnet assembly extending to form a bore into which the anatomy of interest of the patient can be placed, and a plurality of coaxially arranged coils surrounding the bore, the bore having a minimum diameter larger than an axial length of the bore;

positioning means for positioning the patient or said magnet assembly so that the patient is inclined relative to the axis of the magnet assembly and the anatomy of interest of the patient that is to be imaged is positioned in an imaging-field-zone of the magnet assembly at a desired inclination to allow an image to be taken in the desired inclination;

current means for inducing current flow in said coils so as to produce a homogeneous magnetic field in the imaging-field-zone within said bore;

magnetic gradient means for forming gradient magnetic fields in the imaging-field-zone;

RF generating means for generating RF waveforms in the imaging-field-zone;

receiving means for receiving a magnetic resonance signal from the anatomy of interest of the patient in the imaging-field-zone; and processing means for processing the received signal to generate an image of the anatomy of interest of the patient at the desired inclination.

26. A magnetic resonance imaging apparatus according to claim 25, wherein the positioning means comprises translational positioning means for translationally positioning the patient or said magnet assembly so that the patient is in said bore and rotational positioning means for rotating the patient or said magnet assembly about a pivot point on the axis of said bore to maintain the anatomy of interest of the patient in the imaging-field-zone of the magnet assembly and to allow an image to be taken at the desired inclination.

27. A magnetic resonance imaging apparatus according to claim 25, wherein said rotational positioning means is operable to allow the rotation of the patent or said magnet assembly about said pivot point to maintain the anatomy of interest of the patient in the imaging-field-zone of the magnet assembly and to allow an image to be taken in a second desired inclination; said receiving means is adapted to receive a magnetic resonance signal from the anatomy of interest of the patient in the imaging-field-zone at the second desired inclination; and said processing means is adapted to process the received signal to generate a second image of the anatomy of interest of the patient.

28. A magnet assembly for use in a magnetic resonance imaging system for producing a magnetic resonance image of an anatomy of interest of a patient, the assembly comprising:

a bore into which the anatomy of interest of the patient can be placed; and a plurality of coaxially arranged coils surrounding said bore;

wherein said coils are arranged to generate a substantially homogeneous magnetic field in an imaging-field-zone in said bore, and said bore has a minimum diameter substantially larger than the axial length of said bore and a radius of the bore is greater than the a distance from the tip of the head of a human female of average height to the center of the breast of the human female of average height.

* * * * *